US010433754B2

(12) United States Patent
Nurmikko et al.

(10) Patent No.: US 10,433,754 B2
(45) Date of Patent: Oct. 8, 2019

(54) IMPLANTABLE WIRELESS NEURAL DEVICE

(71) Applicant: Brown University, Providence, RI (US)

(72) Inventors: Arto V. Nurmikko, Providence, RI (US); Ming Yin, Providence, RI (US); William R. Patterson, Rehoboth, MA (US); Juan Aceros, Providence, RI (US); David A. Borton, Providence, RI (US); Christopher W. Bull, Rehoboth, MA (US); Farah Laiwalla, Providence, RI (US)

(73) Assignee: Brown University, Providence, RI (US)

( * ) Notice: Subject to any disclaimer, the term of this patent is extended or adjusted under 35 U.S.C. 154(b) by 1475 days.

(21) Appl. No.: 14/028,178

(22) Filed: Sep. 16, 2013

(65) Prior Publication Data
US 2014/0094674 A1 Apr. 3, 2014

Related U.S. Application Data

(63) Continuation of application No. PCT/US2012/029664, filed on Mar. 19, 2012.
(Continued)

(51) Int. Cl.
*A61B 5/0478* (2006.01)
*A61B 5/04* (2006.01)
(Continued)

(52) U.S. Cl.
CPC .......... *A61B 5/0478* (2013.01); *A61B 5/0017* (2013.01); *A61B 5/0031* (2013.01);
(Continued)

(58) Field of Classification Search
CPC ........................... A61N 1/3606; A61B 5/0017
See application file for complete search history.

(56) References Cited

U.S. PATENT DOCUMENTS 7,212,851 B2 5/2007 Donoghue et al.
7,647,097 B2 1/2010 Flaherty et al.
(Continued)

FOREIGN PATENT DOCUMENTS

WO WO-03/061517 A2 7/2003
WO 2008/021524 A2 2/2008

OTHER PUBLICATIONS

Chestek et al., "HermesC: Low-Power Wireless Neural Recording System for Freely Moving Primates," IEEE Transactions on Neural Systems and Rehabilitation Engineering vol. 17, No. 4, pp. 330-338 (2009).
(Continued)

*Primary Examiner* — Alyssa M Alter
(74) *Attorney, Agent, or Firm* — Adler Pollock & Sheehan P.C.

(57) ABSTRACT

Systems and methods for providing an electrical interface to a body are provided. In one embodiment, an implantable module is disclosed, comprising: an implantable electrode array, implantable within a body and capable of providing a plurality of communication channels for communicating electrical signals detected in a body; an amplifier circuit for processing electrical signals received from the electrode array; a wireless transceiver for sending and receiving telemetry data between the amplifier circuit and a wireless receiver located outside of the body; and a sealed enclosure that houses the amplifier circuit and the wireless transmitter and is biocompatible with surrounding tissue, the enclosure having a window that is transparent to a wireless medium used by the wireless transceiver. In another embodiment, a wireless transceiver and amplifier is detachably coupled to a transcutaneous attachment device, and the implantable electrode array is electrically coupled to the interface board via the transcutaneous attachment device.

15 Claims, 36 Drawing Sheets

Related U.S. Application Data

(60) Provisional application No. 61/569,619, filed on Dec. 12, 2011, provisional application No. 61/527,956, filed on Aug. 26, 2011, provisional application No. 61/453,799, filed on Mar. 17, 2011.

(51) Int. Cl.

| | | |
|---|---|---|
| *A61N 1/05* | (2006.01) | |
| *A61N 1/36* | (2006.01) | |
| *A61N 1/372* | (2006.01) | |
| *A61N 1/375* | (2006.01) | |
| *A61N 1/378* | (2006.01) | |
| *A61B 5/00* | (2006.01) | |

(52) U.S. Cl.
CPC ........ *A61B 5/04001* (2013.01); *A61B 5/6864* (2013.01); *A61B 5/6868* (2013.01); *A61N 1/0531* (2013.01); *A61N 1/3606* (2013.01); *A61N 1/375* (2013.01); *A61N 1/3787* (2013.01); *A61N 1/37217* (2013.01); *A61N 1/37223* (2013.01); *A61N 1/37229* (2013.01); *A61N 1/37252* (2013.01); *A61B 2560/045* (2013.01); *A61B 2576/026* (2013.01); *A61N 1/36064* (2013.01); *A61N 1/36125* (2013.01); *A61N 1/3758* (2013.01)

(56) References Cited

U.S. PATENT DOCUMENTS

| | | | |
|---|---|---|---|
| 7,751,877 | B2 | 7/2010 | Flaherty et al. |
| 7,881,780 | B2 | 2/2011 | Flaherty |
| 7,901,368 | B2 | 3/2011 | Flaherty et al. |
| 7,991,461 | B2 | 8/2011 | Flaherty et al. |
| 8,060,194 | B2 | 11/2011 | Flaherty |
| 8,095,209 | B2 | 1/2012 | Flaherty |
| 8,386,050 | B2 | 2/2013 | Donoghue et al. |
| 8,560,041 | B2 | 10/2013 | Flaherty et al. |
| 8,812,096 | B2 | 8/2014 | Flaherty et al. |
| 2002/0099412 | A1 | 7/2002 | Fischell et al. |
| 2005/0143790 | A1* | 6/2005 | Kipke ............... A61B 5/04001 607/60 |
| 2005/0267597 | A1 | 12/2005 | Flaherty et al. |
| 2005/0283203 | A1* | 12/2005 | Flaherty ............. A61B 5/04001 607/48 |
| 2006/0016753 | A1 | 1/2006 | Sowemimo-Coker et al. |
| 2006/0018990 | A1 | 1/2006 | Bazzo et al. |
| 2006/0049957 | A1 | 3/2006 | Surgenor et al. |
| 2006/0058627 | A1 | 3/2006 | Flaherty et al. |
| 2006/0111075 | A1 | 5/2006 | Seol |
| 2006/0149338 | A1 | 7/2006 | Flaherty et al. |
| 2006/0167371 | A1 | 7/2006 | Flaherty et al. |
| 2006/0173259 | A1 | 8/2006 | Flaherty et al. |
| 2006/0195042 | A1 | 8/2006 | Flaherty |
| 2006/0241356 | A1 | 10/2006 | Flaherty |
| 2007/0156126 | A1 | 7/2007 | Flaherty |
| 2007/0169333 | A1 | 7/2007 | Donoghue et al. |
| 2009/0157141 | A1* | 6/2009 | Chiao ............... A61N 1/36071 607/46 |
| 2010/0002302 | A1 | 1/2010 | Duparre et al. |
| 2010/0063411 | A1 | 3/2010 | Donoghue et al. |

OTHER PUBLICATIONS

English Translation of Chinese Office Action dated Mar. 18, 2015 in corresponding Chinese Application No. 201280024098.3 (9 pages).

Extended European Search Report for European Patent Aplication No. 12758264.1 dated Sep. 1, 2014 (9 pages).

Harrison et al., "Wireless Neural Recording With Single Low-Power Integrated Circuit," IEEE Transactions on Neural Systems and Rehabilitation Engineering vol. 17, No. 4, pp. 322-329 (2009).

Harrison et al., "A low-power integrated circuit for a wireless 100-electrode neural recording system," IEEE Journal of Solid-State Circuits vol. 42, No. 1, pp. 123-133 (2007).

Harrison and Charles, "A low-power low-noise CMOS amplifier for neural recording applications," IEEE Journal of Solid-State Circuits, vol. 38, No. 6, pp. 958-965 (2003).

International Search Report and Written Opinion for PCT Application No. PCT/US12/29664 dated Jul. 18, 2012 (9 pages).

Patterson III et al., "CMOS ICs for Brain Implantable Neural Recording Microsystems," Applications of CMOS circuits in Biology, R. Westervelt and H. Lee Eds., pp. 259-291 (Springer, 2007).

Song et al., "A brain implantable microsystem with hybrid RF/IR telemetry for advanced neuroengineering applications," Proc. 29th Ann. Int. Conf. IEEE EMBS, pp. 445-448 (2007).

Song et al., "Development of a chipscale integrated microelectrode/ microelectronic device for brain implantable neuroengineering applications" IEEE Transactions on Neural Systems and Rehabilitation Engineering vol. 13, No. 2, pp. 220-226 (2005).

* cited by examiner

IMPLANTABLE WIRELESS NEURAL DEVICE

CROSS-REFERENCE TO RELATED PATENT APPLICATIONS

This application is a continuation of International Application No. PCT/US2012/029664, filed Mar. 19, 2012, which claims the benefit of priority to U.S. Provisional Patent Application Nos. 61/453,799, filed Mar. 17, 2011, 61/527,956, filed Aug. 26, 2011, and 61/569,619, filed Dec. 12, 2011. The disclosures of these applications are hereby incorporated by reference in their entireties.

GOVERNMENT SUPPORT

The invention was made with United States government support under Grant No. 1R01EB007401-01 awarded by the-National Institute Health, Grant No. 0937848 awarded by the National Science Foundation, and Grant NO. N66001-10-C-2010 awarded by the Defense Advanced Research Project Agency (DARPA). The U.S. Government has certain rights in this invention.

BACKGROUND

This invention relates to implantable wireless devices and methods for using such implants in a body.

A number of approaches exist for retrieving electrical or magnetic signals from the brain of animals and/or humans by use of different neural sensor probes. These may reside outside a subject's head (as in EEG, MEG and fMRI), in a space between the skin and the skull, or below the skull either directly atop the brain or penetrating into the brain. The probes below the skull that reside atop the brain are herewith denoted as electrocorticographic (ECoG) arrays, while those where the individual sensor elements penetrate the brain tissue are denoted as multielectrode arrays (MEAs). While invasive, ECoG and MEAs offer considerably more detailed information about the neural circuit functions than EEG-based approaches. In particular, MEAs have been shown to enable extraction of neural circuit signals with spatial and temporal resolution, in which each individual element (microelectrode) of the array reports from a single neural cell, thereby enabling the retrieval of highly function-specific information. An example would be retrieving information from one hundred neurons whose coordinated operation can issue a specific command for the motion of an arm, hand, or finger.

Considering that the outer skin of a human or animal subject is a protective envelope against the environment, any brain sensors implanted or applied below the skin is considered to be "invasive." Both ECoG and MEA multielectrode implants are examples of invasive probes. With such probes, one major technical challenge is the retrieval of brain signals generated as electrical impulses by appropriate electronic acquisition instrumentation for further interpretation denoted here as decoding. The electronic acquisition instrumentation typically includes analog circuits for signal amplification from the sensor arrays, their subsequent multiplexing (to serialize the data), conversion to digital data stream (A/D conversion), and transmission of the digitized neural data for subsequent signal processing and use. Signal processing involves decoding strategies which employ mathematical models to interpret and convert the brain signals to useful electronic commands that can operate such devices as robotic arms, typewriters, or other external devices directly from commands issued by the subject's brain.

SUMMARY

Brain-machine interfaces are acknowledged to exist in the prior art, and are used to provide brain monitoring in various contexts, such as epilepsy monitoring for patients undergoing assessments of seizure activity using subdural grid electrodes for mapping epileptogenic regions of the brain. However, without the ability to wirelessly transmit data telemetry, such patients are limited to hospital-bed bound stays for up to two weeks for monitoring, with heavy external cables tethering them to external electronics. A wearable, wireless compact device such as the ones disclosed below provide the ability to provide mobility beyond what is possible using cabled connections, and also to allow patients to return home for an extended period of assessment, enabling diagnostic data to be acquired safely and comfortably over a longer time period than is presently feasible.

The concept and implementation is described of an implantable, wireless neural interface device, hereafter referred to as a sub-acute Brown neural card (SBNC), which enables communication between the brain and external world, where the "external world" is composed of any number of electronically controlled devices and device systems.

Systems and methods for providing an electrical interface to a body are provided. In one embodiment, an implantable system for providing an electrical interface to a body is disclosed, comprising: an implantable electrode array, implantable within a body and capable of providing a plurality of communication channels for communicating electrical signals detected in a body; an interface board coupled to the electrode array for providing a fan-out of electrical wires to a plurality of electrical contacts; an amplifier circuit coupled with the plurality of electrical contacts for processing electrical signals received from the electrode array into data signals; a wireless transceiver coupled to the amplifier circuit for sending and receiving telemetry data between the amplifier circuit and a wireless receiver located outside of the body; a sealed enclosure that houses the amplifier circuit and the wireless transmitter and is biocompatible with surrounding tissue; and a window within the enclosure that is transparent to a wireless medium used by the wireless transceiver, wherein the wireless transceiver is capable of sending data from the plurality of communication channels.

In another embodiment, a system for providing an electrical interface to a body is disclosed, comprising: an implantable electrode array, implantable within a body and capable of providing a plurality of communication channels for communicating electrical signals detected in a body; an interface board electrically coupled to the implantable electrode array for providing a plurality of electrical contacts for the implantable electrode array; an amplifier circuit coupled with the interface board for processing electrical signals received from the electrode array into data signals; a wireless transceiver coupled to the amplifier circuit for sending and receiving telemetry data between the amplifier circuit and an external wireless device located outside of the body; a housing external to the body that houses the interface board, the amplifier circuit, and the wireless transceiver; and a percutaneous attachment device, wherein the housing is detachably coupled to the percutaneous attachment device, wherein the implantable electrode array is electrically coupled to the interface board via the percutaneous attachment device, and wherein the wireless transceiver is capable of sending data from the plurality of communication channels.

In another embodiment, a system for providing an electrical interface to a body is disclosed, comprising: an interface board electrically coupled to an implantable electrode array; an amplifier circuit coupled with the interface board for processing electrical signals received from the electrode array into data signals; a wireless transceiver coupled to the amplifier circuit for sending and receiving telemetry data between the amplifier circuit and an external wireless device located outside of the body; and a housing external to the body that houses the interface board, the amplifier circuit, and the wireless transceiver, wherein the housing is detachably coupled to a percutaneous attachment device, and wherein the wireless transceiver is capable of sending data from the plurality of communication channels.

In another embodiment, a method for detecting an electrical signal in a body is disclosed, comprising: detecting a plurality of electrical signals at a microelectrode array implanted in a body; receiving the plurality of electrical signals from the microelectrode array at a sealed enclosure implanted within the body and electrically coupled to the microelectrode array; processing the electrical signals within the enclosure to produce a plurality of channels of amplified data signals; and transmitting the plurality of channels via a wireless medium through a window within the enclosure, the window transparent to the wireless medium.

In another embodiment, a method for detecting an electrical signal in a body, comprising: attaching a processing module to an exterior of a body at a percutaneous attachment device; electrically coupling the processing module to a microelectrode array implanted in the body; detecting a plurality of electrical signals from a plurality of neurons at the microelectrode array within the body; receiving the plurality of electrical signals from the microelectrode array at the processing module external to the body; processing the electrical signals within the processing module to produce a plurality of channels of amplified data signals; and transmitting the plurality of channels via a wireless medium to a wireless device external to the processing module.

DETAILED DESCRIPTION

Figure 1:
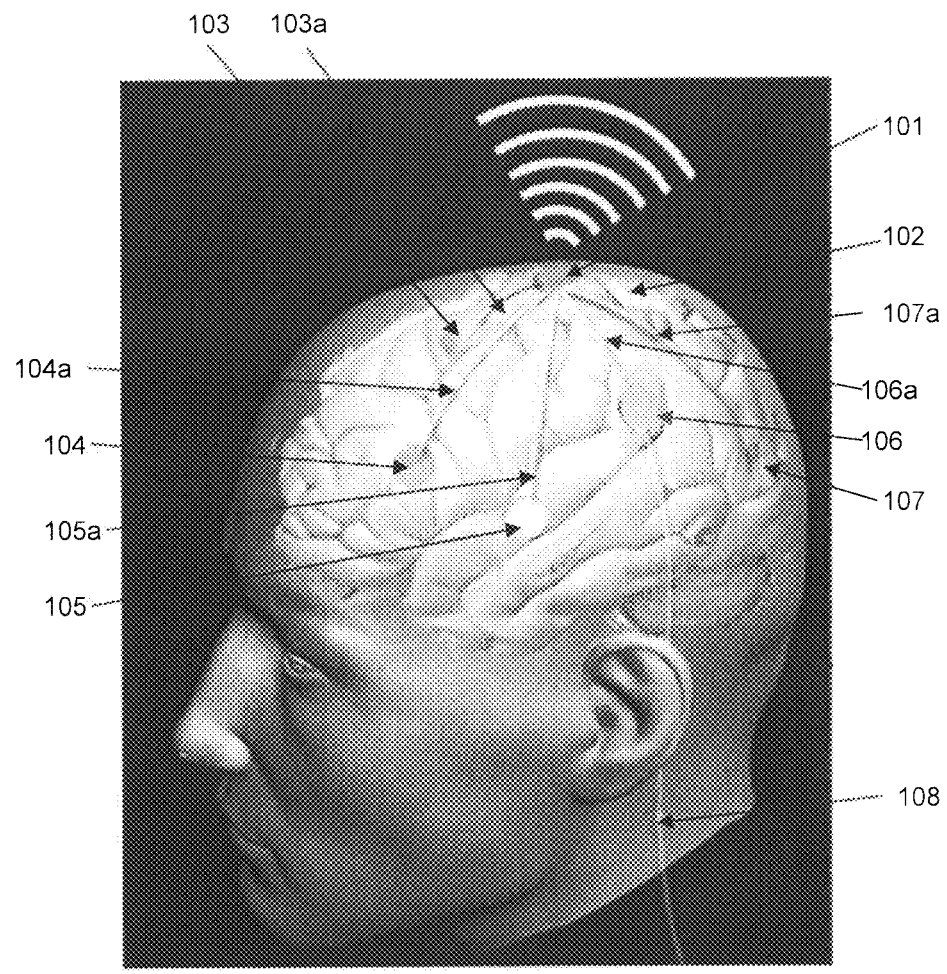
FIG. 1 is a cutaway diagram of an SBNC system situated within a subject's brain, in accordance with some embodiments.

The present application describes a hermetically-sealed module for chronic implant in the subject's head or elsewhere in the body or an externally mounted module that provides wireless data communications capability, both of which referred to as a sub-acute Brown neural card (SBNC). The SBNC presents a device system for implantable wireless brain interfaces useful for neural signal extraction. Neural stimulation and in-situ physical/physiological monitoring capabilities may further be added, for enabling bidirectional communication between brain circuits and those in the external world.

In one aspect, a SBNC module that incorporates batteries, amplifiers and other circuitry may be hermetically sealed and implanted below the skin of a subject in the head area, or elsewhere in the body. The device may be either physically wired or wirelessly linked to one or more multi-element neural sensors which interact electronically with the brain's own neural circuits. The neural sensors can be devices that transmit electrical or optical signals to provide a measure of a brain circuit's activity. These signals are routed to the SBNC module, which has several attributes, including internal microelectronic chip-scale circuits that amplify, digitize, and control the neural signal data flow from the brain to the onboard radio-frequency and/or infra-red emitter for transmission through the subject's (naturally sealed) skin.

In another aspect, the device also may house microelectronic chip-level elements that enable neural stimulation in form of electrical excitation to be applied to the multi-element neural sensor, now acting as a neural stimulator. The device has the ability to apply selected geometrically-defined spatial patterns of neural stimulation across neural populations engaged in relevant brain activity, while controlling this patterned multichannel stimulation with timed stimulus of each individual element in the neural sensor/stimulation cortical microelectrode array. Finally, the device may also contain neural sensor array circuitry for concurrently delivering other physiologically-relevant information about the neural circuit environment, including microscale local temperature and pressure variation, thereby enabling the module to monitor metabolic activity of the target neurons.

In some embodiments, the device is capable of both measurement of neuronal activity and neural stimulation.

In one embodiment, a multifunctional SBNC device includes multiple dedicated electronics assemblies, embodied within a hermetically-sealed, biocompatible implantable module.

In certain embodiments, the electronic acquisition instrumentation which reads out the brain signals from the brain sensors are configured as miniaturized, body implantable modules which amplify, multiplex and A/D convert such brain signals, and transmit the digitized neural data by streaming wirelessly through the skin to an external receiver in real time. The SBNC can be implanted either in the head or elsewhere in the body so that the digital neural signal data stream can be wirelessly transmitted through the skin ("transcutaneously") without the need to physically cable the signals through the skin ("percutaneously"). Wireless transmission also enables unrestricted mobility for a subject, whereas conventional electronic cabling is a serious impediment to subject movement due to the tethering of the subject to external electronic modules.

Another use for brain compatible electrodes is in applying electrical stimuli to specified target areas of the brain, with deep brain stimulation (DBS) being the best-known. The SBNC can integrate both neural signal retrieval and electrical stimulation within a single hermetically-sealed wireless module.

Circuitry within the SBNC may enable monitoring local physical and physiological state of brain tissue at up to single-neuron spatial resolution. Such in-situ diagnostic monitoring provides several features, such as allowing for monitoring single neural cell activity subject to significant variations due to intrinsic neural circuit variability (non-stationary behavior), neural cell health over long periods of time, and possible physiological interactions between an implanted neural sensor (MEA, ECoG) and brain and body tissue. A typical neuron generates 10-100 spikes per second when active, or 1-10 spikes per second in a resting state; these spikes can be detected as electrical action potentials by the individual microelectrodes situated in nearby extracellular fluid surrounding the neuron. The SBNC is capable of capturing and recording broadband neural signals. These broadband neural signals can include the entire range of frequencies covered by the different temporal signatures of the neural signals. For example, the broadband capture of temporal signatures include so-called Action Potentials (or 'spikes') on a millisecond timescale, so-called Field Potentials which typically range from anywhere from a few tens of milliseconds to a fraction of a second, rhythmic oscillations in the form of the so-called alpha, beta, gamma, and delta bands ('brain waves'), time variations induced by metabolic activity associated with the neurons, and so on. In some embodiments, the SBNC can selectively capture all neurologically and physiologically meaningful signals over a wide range of time signatures (translating in frequency units from about 10 KHz to 0.1 Hz). MEA or ECoG electrode systems contemplated for use in some embodiments are capable of providing real-time data rates of up to 50 Mb/sec, and the present system provides the ability to process this data prior to transmission at a high data rate.

FIG. 1 is a cutaway diagram that illustrates an implant system including the SBNC according to some embodiments. The cutaway perspective diagram shows a representative human with the brain visible beneath the skull. An implanted electronic device 101, which is a SBNC unit, is shown wirelessly transmitting data to a device (not shown) external to the skull. Device 101 may be implanted exterior to the skull. Other implanted electronic devices 103, 104, 105, 106, 107 are also shown, each implanted in a different part of the brain 102 and connected via wires 103a, 104a, 105a, 106a, 107a to the implanted electronic device 101, which contains an amplifier device. The wires may be individual multi-wire bundles. Each implanted device 103, 104, 105, 106, 107 includes a multi-electrode array for direct capture and recordation of brain signals at the area of the brain to the implant. The implanted arrays may be MEA or ECoG cortical sensor arrays or other electrode sensors as are known or used in the art. The multi-wire bundle may be microwires that correspond in number to the number of sensor elements in each MEA or ECoG cortical sensor array, and may be made of a biocompatible conductor such as gold. The proximal end of the wire bundle may be connected to the hermetically-sealed SBNC unit which is to be implanted below the skin of the subject, either in the head or elsewhere in the body. The implanted devices 103, 104, 105, 106, 107 may also share the wireless transmitter of implanted SBNC unit 101, thereby being enabled to transmit their data outside of the body. It is possible for an implanted device to also provide an external wired interface, as shown by wire 108 emerging from implanted device 106. The wired interface may be electrical or optical.

Figure 2:
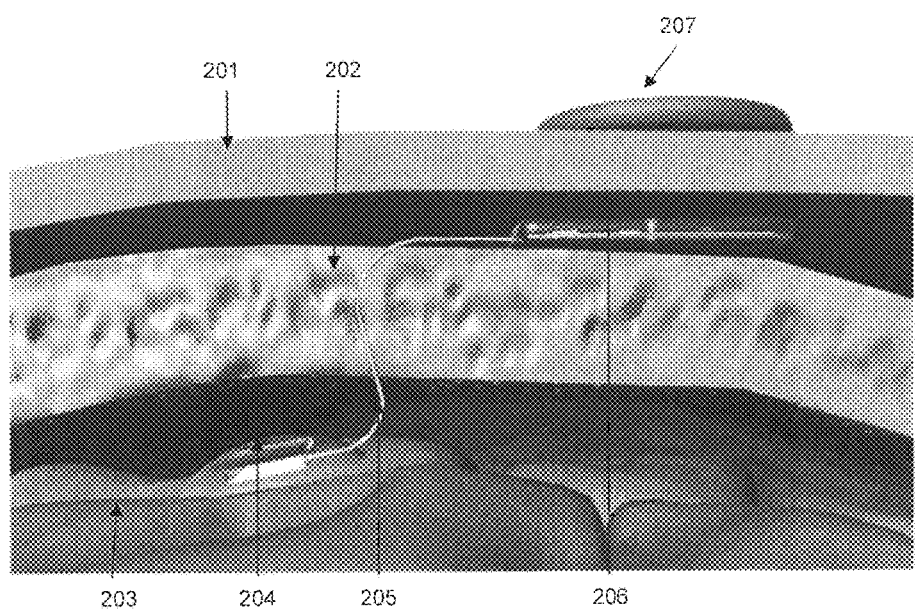
FIG. 2 is a profile cutaway diagram of an SBNC system situated within a subject's brain, in accordance with some embodiments.

FIG. 2 shows a profile cutaway view of an SBNC module and sensor array implanted within the skull, in accordance with some embodiments. Skin 201, cranium 202 and brain matter 203 are shown. Also shown is an electrode array 204, connected via a multi-wire bundle 205 to implanted SBNC device 206. Also shown is device 207, which is located external to the skull and skin and which is wirelessly connected to implanted SBNC device 206 for providing both power and data connectivity. Multi-wire bundle 205 passes through a channel in the skull and uses a biocompatible material in order to minimize adverse reactions within the body. In some embodiments, preserving the integrity of the outer skin layer and wirelessly transmitting power and data minimizes the risk of infection that would be the result of an open port into the body.

In another aspect, a compact unit containing electronics may be attached externally to a subject's head, e.g., by mating onto a skull-mounted pedestal or other percutaneous attachment device. This aspect may be referred to as the external Brown Neural Card (E-BNC). The pedestal in turn provides a pass-through port for wiring from below the subject's skin through the skull to an implanted intracortical or epicortical multielectrode array. The implanted array may be capable of data reception, transmission and recording from brain microcircuits and their electrical impulses via physical wires that are passed through the wiring port. The device may be capable of 100 channels for neural broadband data in recording and stimulation (from <1 Hz to 10 kHz), and may be scalable to hundreds of such independent neural data channels. The device may be capable of interfacing wirelessly with other external devices to enable mobility. A specific compact configuration is also disclosed which can be employed by animal and human subjects to access brain circuits using a lightweight, battery-powered, easily-detachable modular unit.

The E-BNC system may employ a "screw-top" interface for mating the skull-mounted pedestal to an electronics assembly and battery array/battery pack. Other mechanisms may be used in addition to or in place of the screw threading mechanism, such as a tongue-and-groove mechanism, a magnetic seal, a spring-loaded latch mechanism, or others. The electronics assembly may include an amplifier printed circuit board (PCB) and a wireless transmitter board, among other components. A battery pack may be provided in the housing. The battery pack may be detachable. The battery array may be implemented as a series of batteries in a ring configuration, with a press-fit ball locking assembly configured to mate to the electronics assembly providing quick attachment/detachment. The locking assembly is configured with the electronics assembly oriented in the center and the battery pack surrounding the electronics assembly. Multiple battery packs may be attached together to the device to provide extended operational time. The system need not be hermetically-sealed, which may be advantageous for factors such as cost and manufacturing tolerances.

Figure 3:
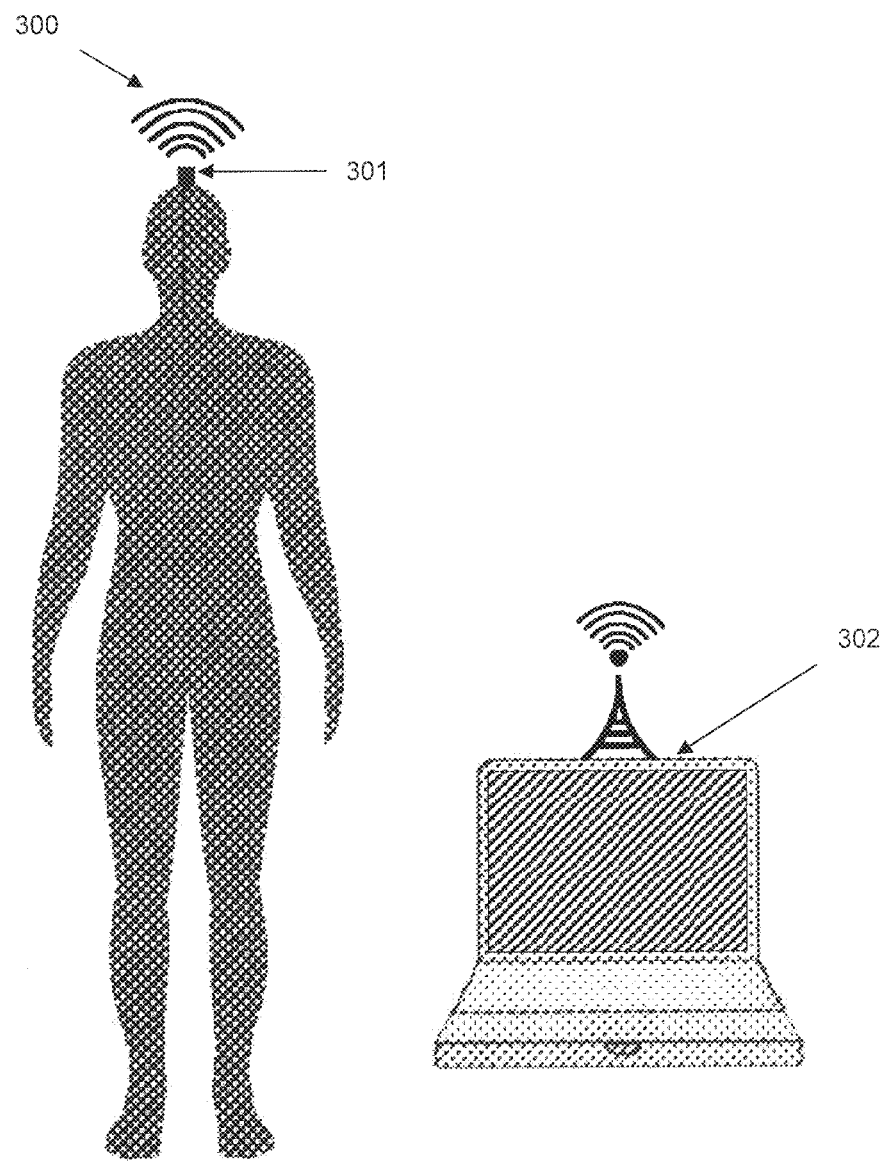
FIG. 3 is a representative diagram of an SBNC system interoperating with an external computer system, in accordance with some embodiments.

FIG. 3 shows a representative diagram of an SBNC system interoperating with an external computer system, in accordance with some embodiments. The SBNC system 300 includes an implanted electrode array (not shown) that samples brain activity, as described elsewhere herein. The implanted electrode array may be connected via a multi-wire bundle or via a wireless data connection to a head-mounted SBNC module 301, which may either be an implanted SBNC module containing amplifiers for connecting to the implanted electrode array, or an external neural interface module. Module 301 may contain wireless charging and communications capability for interfacing with an implanted SBNC module (not shown). Module 301 contains wireless communication capability for communicating with computer 302 via a short-range wireless interface such as Bluetooth, or 802.11 WiFi, or another wireless interface. Computer 302 may also execute software for receiving or transmitting information to and from the SBNC modules.

Figure 4:
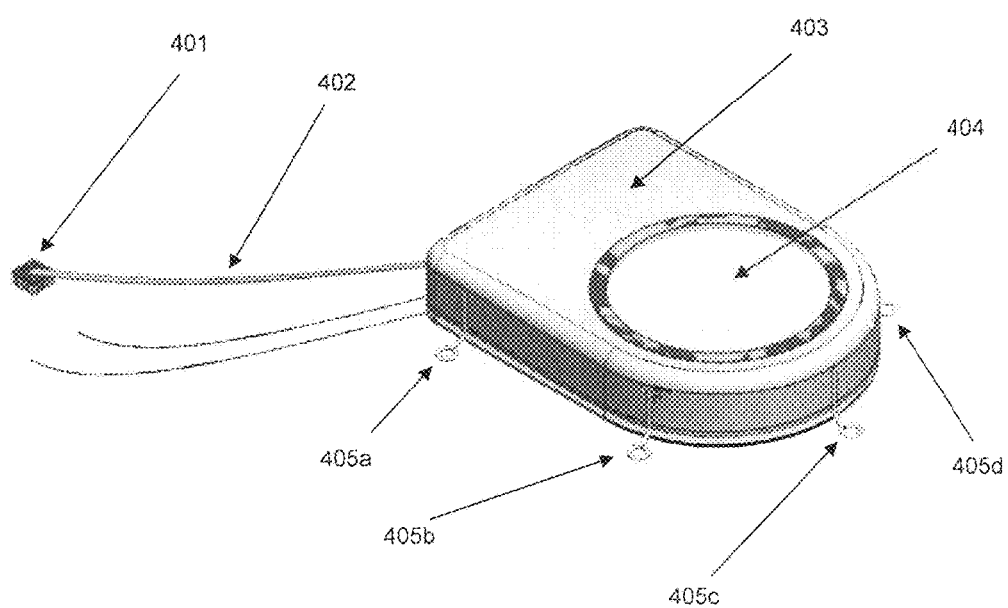
FIG. 4 is an external view of an implantable SBNC module, in accordance with some embodiments.

FIG. 4 shows an external view of an implantable SBNC module, in accordance with some embodiments. Sensor array 401, for implantation into the cerebral cortex, is attached to the distal end of wire bundle 402. The proximal end of wire bundle 402 is connected to a hermetically-sealed titanium welded enclosure 403, referred to as the "Ti-can," according to certain embodiments. Other metals or structural materials may also be used. The top of the Ti-can 403 may have a hermetically-sealed single crystal sapphire window 404 for electromagnetic and optical transparency. Anchors 405a, 405b, 405c, 405d may be used to secure Ti-can 403 to the brain or to other structures within the body.

Figure 5:
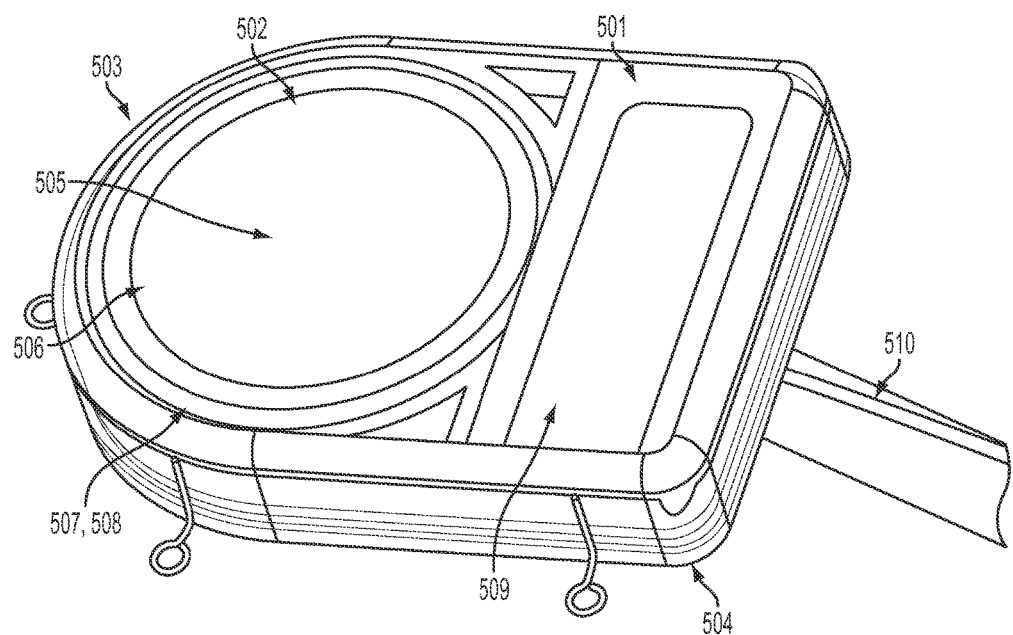
FIG. 5 is a detailed external view of the physical structure of an SBNC, in accordance with some embodiments.

FIG. 5 shows a detailed external view of the physical structure of an SBNC, in accordance with some embodiments. Hermetically-sealed titanium welded enclosure 501 contains the components included in the SBNC. In its hermetically sealed titanium enclosure, which houses all active analog and digital circuits as well as the wireless transmitter and battery, the system may operate continuously with a battery recharge performed wirelessly at periodic intervals, e.g., every 8 hours, or as needed. On the right of the figure is a protective holder for the MEA array/cortical sensor array. Not shown is an assembly that is used on the exterior of the skull that provides wireless recharging power to the SBNC.

The enclosure includes two parts, referred to here as top 503 and bottom 504. The top of the Ti-can 503 may have a hermetically sealed single crystal sapphire window 502 for electromagnetic and optical transparency. This window 502 provides electromagnetic and optical transparency for components within the SBNC. A polymer sheath or case may also be used for various components, including interconnect wiring. The window 502 may facilitate one or more of the following: (i) low-loss transmission of radio/microwave and/or infrared carrier-encoded neural and other monitored data wirelessly from the SBNC; (ii) sending radio-frequency power into the SBNC via inductive coupling for recharging the embedded battery source; and (iii) sending command signals via radio frequency link to the SBNC for neural stimulation. A RF transmission antenna 505, interior to the Ti-can, may provide signal out capability, and an RF receiving coil 506 may provide signal in capability and/or power in capability in some embodiments. Two stacked PCB boards on flexible substrates, PCB-A 507 and PCB-B 508, provide the electronics. Power may be provided by one, two or another number of rechargeable battery modules 509, which may be Quallion QL0200I-A lithium ion 200 mA batteries. Wire bundle 510 is sandwiched between top 503 and bottom 504 and is connected to sensor array 401 (not shown).

The bottom of the Ti-can may include an array of metal-to-ceramic feedthrough pins laid out in such a way that their density (for e.g. a 100-element MEA or ECoG sensor) can accommodate a corresponding number of hermetically tight seals for the spatially-arrayed pins within available manufacturing techniques.

Figure 6:
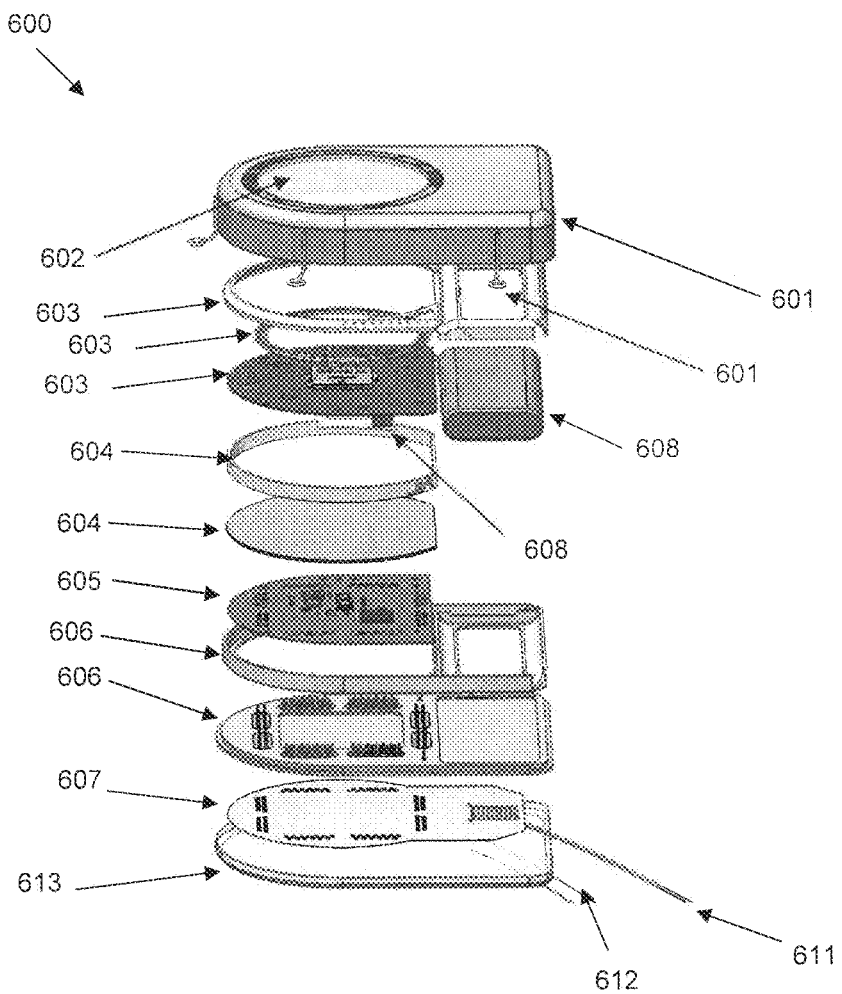
FIG. 6 is an exploded perspective diagram of the primary elements of an SBNC module, in accordance with some embodiments.

FIG. 6 is a second exploded perspective diagram of another embodiment of an SBNC module, in accordance with some embodiments. These components are interconnected and nested in a close-packed, layered and intercalated form factor. The arrangement of components may enable a low profile for the overall thickness of the SBNC subcutaneous implant for surgical implantation into animal and human subjects. The architecture and component placement and integration inside the Ti-can may also allow the SBNC device to be implanted.

In FIG. 6, external fixation elites 601 are connected to top of hermetically-sealed titanium canister (Ti-can) 603, which also contains a sapphire window 602 that is transparent to both optical and radio frequency signals. The Ti-can 603 is coupled with top nesting structure 604. Under the nesting structure is RF power/data printed circuit board (PCB) 605, holding RF transceiver and antenna and inductive charging coil, which in turn sits on middle nesting structure 606. Medical-grade Li-polymer rechargeable battery 608 is coupled to both RF board 605, also called PCB-B, and amplifier board 609, also called PCB-A, which sits below electrical/electromagnetic spacer/shield 607, which may be made of copper or other compatible material. Spacer 607 prevents unwanted crosstalk between PCB-A and PCB-B. The battery is coupled with bottom nesting structure 610, which in turn sits on bottom Ti-can 611. Bottom Ti-can 611 has feed-through holes that allow wires to pass through to parallel interconnect plate (PIP) 612, which is immediately below bottom Ti-can 611. The Ti-enclosure may contain additional micromechanical supporting structures to facilitate the dense, nested packing of all the electronically functional elements listed above. Additional electrical wiring may also be provided. A single lithium polymer rechargeable battery 608 is shown in FIG. 6, but two or more batteries may also be provided.

Also shown in FIG. 6, parallel interface plate (PIP) 610 may facilitate the electrical conduit from the individual wires of the incoming bundle 611. PIP 610 may be made of a thin flexible polymer substrate material such as Kapton, within which the fan-out wiring is embedded (see the very thin multiple traces in FIG. 13). While the Ti-can may be hermetically sealed by welding methods, the PIP may be overmolded by silicone or a comparable biocompatible polymer for protection of its internal wiring from ionically-conducting body liquids. Wires from the bundle may fan out onto the PIP by the wirebonding of the individual wires to specific PIP sites at holes commensurate with alignment, and by compressing the PIP onto the bottom Ti-can so as to provide electrical contact to the feedthrough pins. The wire bundle may be coated in, or made of, gold or other electrically conductive metals. Reference wires made of platinum, iridium, or other biocompatible conductors may also be provided.

Amplifier board 609 may be a flexible printed circuit board, labeled PCB-A, which enables electrical routing and wiring of the incoming neural signals as mapped inputs to custom analog microelectronic chips, and also interconnects, outputs, and handles control and communication and analog-to-digital conversion as dedicated digital chips. RF board 605 may be another flexible printed circuit board, labeled PCB-B, which handles radio, microwave, infrared, electromagnetic, or other wireless communication and powering transcutaneously, which may be made of Kapton.

Figure 7A:
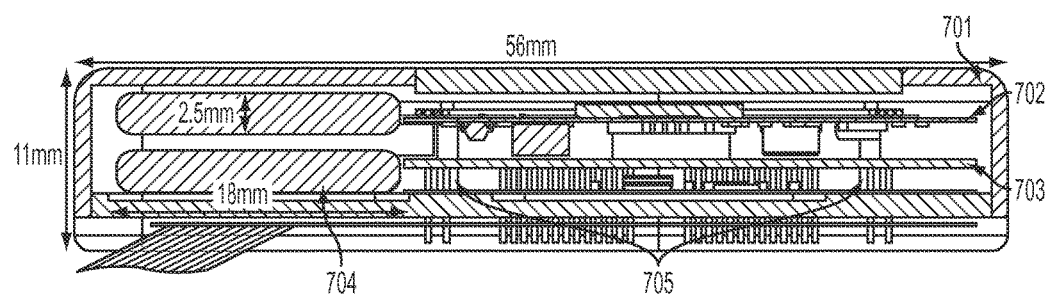
FIGS. 7A and 7B are cross-sectional views of an SBNC module, in accordance with some embodiments.
Figure 7B:
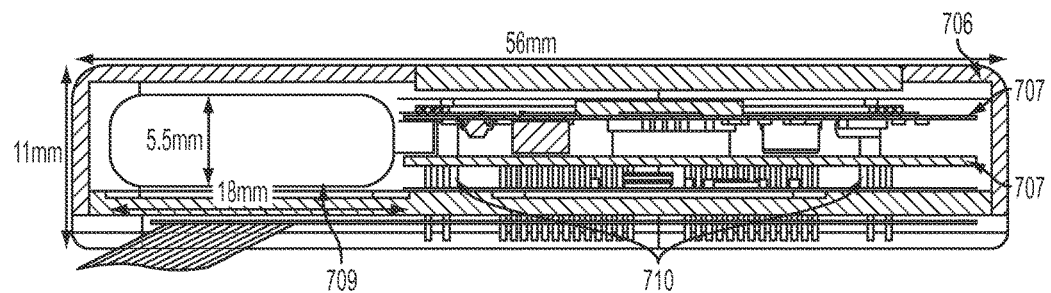

FIGS. 7A and 7B are cross-sectional views of an SBNC module, in accordance with some embodiments. Ti-can 701 and 706 are exterior to a number of components, including RF board 702, 707 and amplifier board 703, 708. Spacer posts 705, 710 are shown in the cross-sectional views. FIG. 7A shows a dual-battery configuration, which may use a pair of custom batteries 704 with 120 mAh from EEMB Co., Ltd. FIG. 7B shows a single-battery configuration, which could use the Quallion QL0200IA, with a capacity of 200 mAh. Alternatively, other batteries could be used that would satisfy minimum battery capacity and maximum physical size requirements. As the battery is fully-implanted, a battery may be provided for providing approximately seven hours of battery life. A battery with up to 24 hours of battery life and beyond is also possible in some embodiments.

The electronic circuits which occupy the boards PCB-A and PCB-B, respectively, are described in terms of their subcomponent circuits and microelectronic chips and their corresponding functionality.

Figure 8:
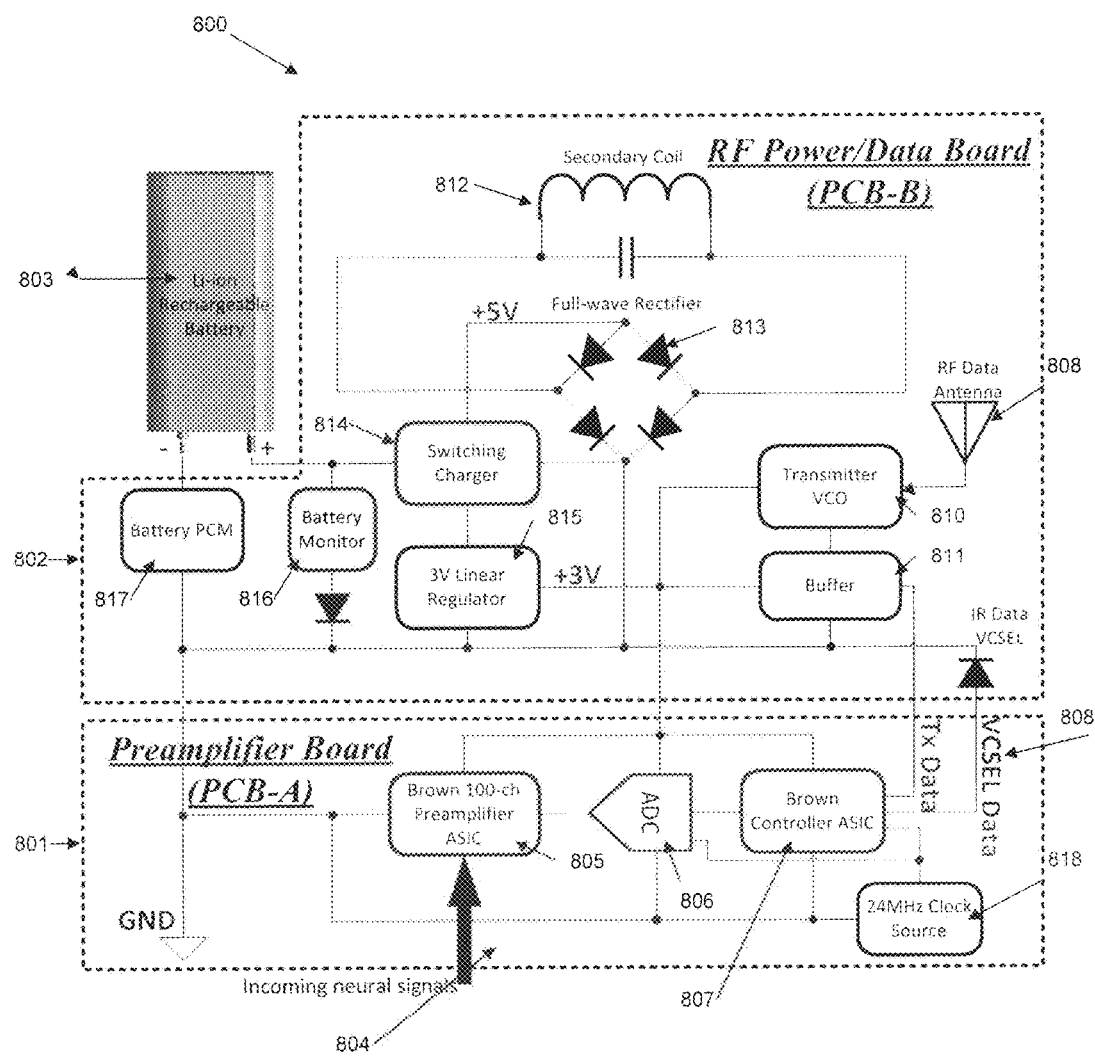
FIG. 8 is a circuit block diagram for a RF power/data board and preamplifier board, in accordance with some embodiments.

FIG. 8 shows a circuit block diagram 800 for PCB-A 801, PCB-B 802, and the battery 803 that are inside of the SBNC Ti-enclosure (not shown), according to certain embodiments. The signal flow of the electronics is as follows. An incoming neural signal 804 acquired by the electrode array is passed to the PCB-A though the wire bundle, the PIP, and the feedthroughs on the bottom of the Ti-enclosure. After entering the PCB-A, the neural signals are amplified by a preamplifier ASIC chip 805. The amplified neural signals are then digitized and packaged by one or more successive approximation analog-to-digital converters (ADCs) 806 and a controller ASIC chip 807, respectively. The controller chip sends the packaged digital data in either TTL or VCSEL drive format 808, which can drive the RF transmitter 809 or the infrared laser (not shown) on the PCB-B board for wirelessly transferring the neural data to the external receiving unit. The transmitter VCO 810 and buffer 811 are used for the wireless data antenna 809. Except for these two connections, PCB-A and PCB-B may also share a common ground and a 3V supply voltage. The PCB-B may also incorporate a wireless Li-ion battery recharging circuit that harvests RF power from the external charging unit for the SBNC. Shown for this purpose are a secondary coil 812, a full-wave rectifier 813, a switching charger 814 and 3V linear regulator 815, a battery monitor 816, and a battery protection circuit module (PCM) 817. Also present is 24 MHz clock source 818.

Figure 9:
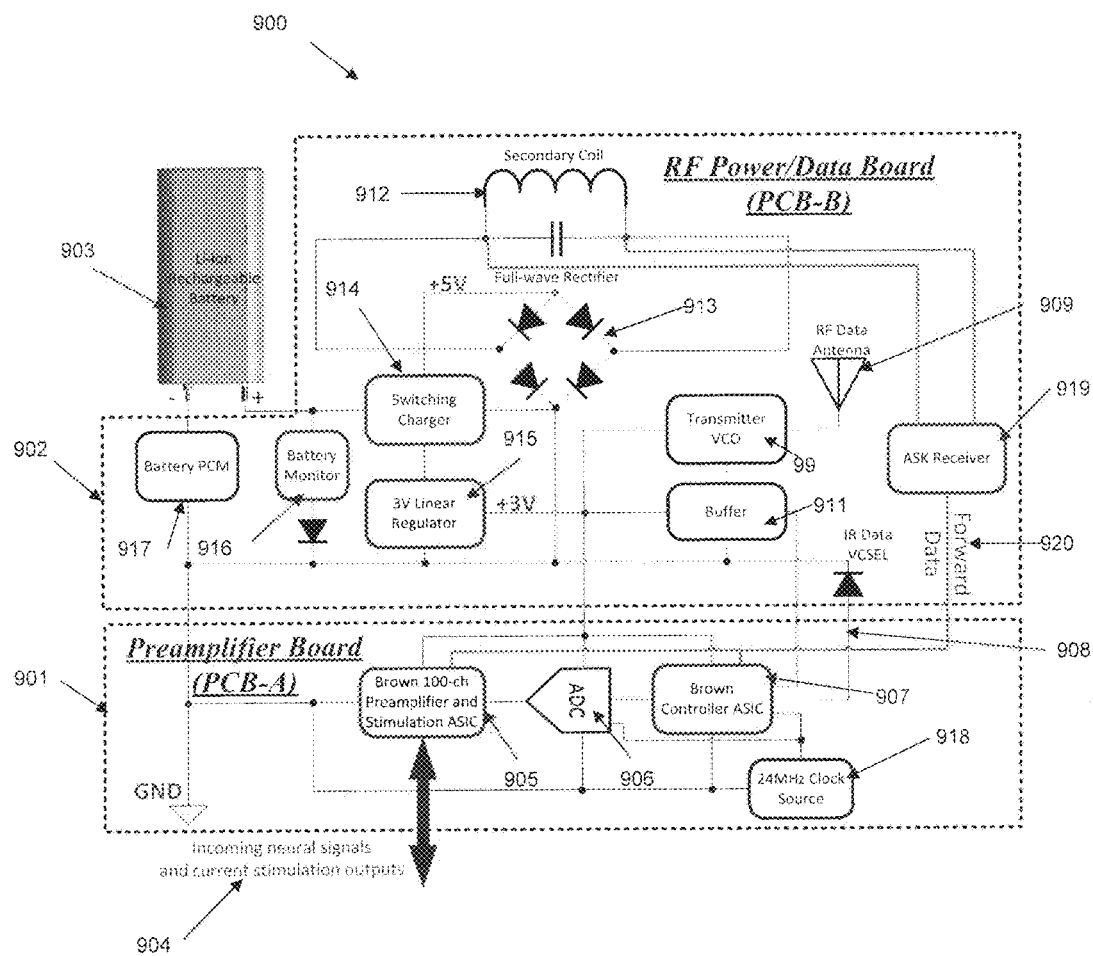
FIG. 9 is a circuit block diagram for a RF power/data board and preamplifier board in a forward data configuration, in accordance with some embodiments.

FIG. 9 shows a circuit block diagram 900 for PCB-A 901, PCB-B 902, and the battery 903 that are inside of the SBNC Ti-enclosure (not shown), according to certain embodiments. The circuit block diagram 900 of FIG. 9 is similar to circuit block diagram 900 of FIG. 9, with the addition of a forward data path that allows data to be received from an external wireless connection and sent as current stimulation outputs to the electrode microarray (not shown) via preamplifier board PCB-A 901. Neural signals 904 may be incoming signals or outgoing current stimulation outputs, which are received from or output to the electrode array, respectively. Preamplifier ASIC chip 905 is modified to allow for modulation of electrical signals into neural signal outputs, in addition to performing preamplification of received neural signals. ADCs 906 and a custom design controller ASIC chip 907 perform signal conversion for the received neural data. Forward data 920 is provided directly to preamplifier ASIC chip 905 from PCB-B. TTL or VCSEL drive format 908 is used for sending received neural data from PCB-A to PCB-B, as it can drive the RF transmitter 909 or the infrared laser (not shown) on PCB-B. Transmitter VCO 99 and buffer 911 are used for the wireless data antenna 909. The battery recharging circuit components, which include secondary coil 912, a full-wave rectifier 913, a switching charger 914 and 3V linear regulator 915, a battery monitor 916, and a battery PCM 917, provide recharging capability as described above. In some embodiments, ASK receiver 919 is connected to secondary coil 912, and is used to receive data from external sources using the secondary coil. This data may be subsequently transmitted via the forward data connection as current stimulation outputs 904 to the microelectrode array. In other embodiments, ASK receiver 919 may be connected to RF data antenna 909. A clock source 918 is also provided.

To provide the additional forward data features above, the SBNC may also implement one or more of: multichannel programmable neural stimulation; in-situ impedance spectroscopy on MEAs and ECoGs; metrology of physiological indicators; current stimulation for each channel through the same recording electrodes; impedance spectroscopy for each channel to monitor the impedance change of each electrode; a wireless receiver to receive stimulation and impedance spectroscopy commands, in some embodiments.

Figure 10:
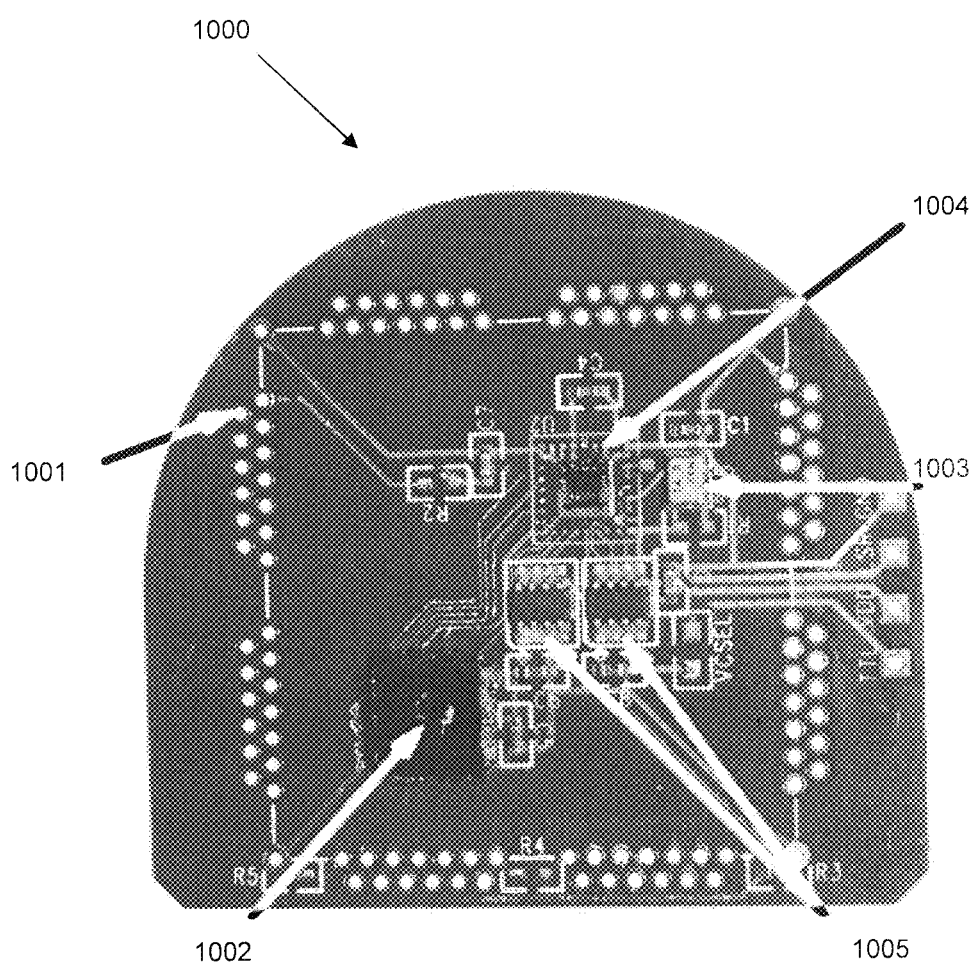
FIG. 10 is a representative view of a preamplifier board, in accordance with some embodiments.

FIG. 10 shows the layout of functional circuit elements and microchips on PCB-A according to some embodiments. Integrated circuit board PCB-A houses ultralow power preamplifiers for broadband neural signals for each of the incoming channels, providing a total number of channels of at least 100 in some embodiments, with each channel corresponding to a micro-electrode array (MEA) or electrocorticographic (ECoG) individual electrodes. Broadband neural signals refer to signals whose frequency domain content spans 0.1 Hz to 10 kHz. These signals may be used to capture events such as action potentials, field potentials, and low frequency activity in the brain.

The PCB-A unit also houses multiplexing circuitry on a single chip to serialize data for its subsequent electrical routing to the PCB-B, which can be of the type known in the art. The ultralow power analog preamplifiers may be preamplifiers such as reported by R. R. Harrison and C. Charles, "A low-power low-noise CMOS amplifier for neural recording applications," IEEE Journal of Solid-State Circuits, 38: 958-965, June 2003; and R. R. Harrison, P. T. Watkins, R. J. Kier, R. O. Lovejoy, D. J. Black, B. Greger, F. Solzbacher, "A low-power integrated circuit for a wireless 100-electrode neural recording system", IEEE J Solid-State Circuits.; 42(1):123-133 January 2007, as well as independently by the Brown University team in Y.-K. Song, W. R. Patterson, C. W. Bull, J. Beals, N. Hwang, A. P. Deangelis, C. Lay, J. L McKay, A. V. Nurmikko, M. R. Fellows, J. D. Simeral, J. P. Donoghue, and B. W. Connors, "Development of a chipscale integrated microelectrode/microelectronic device for brain implantable neuroengineering applications", IEEE Trans Neural Syst and Rehabil Eng, 13(2): 220-226, 2005; and Y. Song, W. R. Patterson, C. W. Bull, D. A. Borton, Y. Li, A. V. Nurmikko, J. D. Simeral, and J. P. Donoghue, "A brain implantable microsystem with hybrid RF/IR telemetry for advanced neuroengineering applications", Proc. 29th Ann. Int. Conf. IEEE EMBS, pp. 445-448, August 2007.; "CMOS ICs for Brain Implantable Neural Recording Microsystems", William R. Patterson III, Y. K Song, C. Bull, F. Laiwalla, Arto Nurmikko, and J. P. Donoghue, in Applications of CMOS circuits in Biology, R. Westervelt and H. Lee Eds. (Springer 2007), pp. 259-29;. Likewise, the multiplexer chip may be an integrated circuit such as that reported previously (Y. K. Song, above). These citations are hereby incorporated by reference.

Internal layout wiring embedded within PCB-A 1000 is designed and physically embodied is such a manner that independent signals from elements of the neural sensor (MEA, ECoG) which enter the hermetically sealed Ti-enclosure through a feedthrough array of electrically isolated pins 1001 are redistributed in a fanout and routing pattern so that the electrical neural signals converge to inputs of a compact preamplifier chip 1102. A clock source 1003 is also shown.

Other microelectronic circuit chips in PCB-A include a specifically designed digital control and command unit 1004 which may provide timing and distribution of the amplified neural signals while preparing and directing the arriving analog signals to the inputs of one or more analog-to-digital converter chips (A/D circuit) 1005 also embedded into PCB-A. Exemplary command and control chip include a microelectronic circuit design as described by Y.-K. Song, W. R. Patterson, C. W. Bull, J. Beals, N. Hwang, A. P. Deangelis, C. Lay, J. L McKay, A. V. Nurmikko, M. R. Fellows, J. D. Simeral, J. P. Donoghue, and B. W. Connors, "Development of a chipscale integrated microelectrode/microelectronic device for brain implantable neuroengineering applications", IEEE Trans Neural Syst and Rehabil Eng, 13(2): 220-226, 2005; Y. Song, W. R. Patterson, C. W. Bull, D. A. Borton, Y. Li, A. V. Nurmikko, J. D. Simeral, and J. P. Donoghue, "A brain implantable microsystem with hybrid RF/IR telemetry for advanced neuroengineering applications", Proc. 29th Ann. Int. Conf. IEEE EMBS, pp. 445-448, August 2007.; "CMOS ICs for Brain Implantable Neural Recording Microsystems", William R. Patterson III, Y. K Song, C. Bull, F. Laiwalla, Arto Nurmikko, and J. P. Donoghue, in Applications of CMOS circuits in Biology, R. Westervelt and H. Lee Eds. (Springer 2007), pp. 259-29. These references are hereby incorporated by reference.

The A/D chip, which follows in its design and internal configuration other prior state-of-art high end 12 or 16-bit A/D converters, operates in concert with the digital controller chip to intermediate communication and signal flow between PCB-A and PCB-B, and within PCB-A itself, as well as receiving external control signals from outside (the body) electronics, where such external command signals are first received wirelessly by other telemetry circuit elements integrated within PCB-B (see below). It may provide either 12-bit or 16-bit resolution, and sampling rates between 20 and 40 thousand samples per second per channel (20-40 kSps/Ch). Combined, the overall system may process between 24 and 64 megabits per second (Mbps).

In some embodiments, the SBNC provides electronic function, integration and spatial arrangement of the individual components on the PCB-A, particularly in the context of connectivity matching with other functional elements in the SBNC. These other functional elements can include the PIP, Ti-can feedthrough pin layout, and other features that provide electrical connectivity to PCB-B and the battery. The SBNC also allows for the stacking compatibility of the PCB-A as a geometrically planar, thin constituent layer for the overall nested arrangement of all the electrically functional units which compose the SBNC as shown in, e.g., FIGS. 5, 6, and 7. The SBNC also provides the elements and functions of PCB-B.

Figure 11:
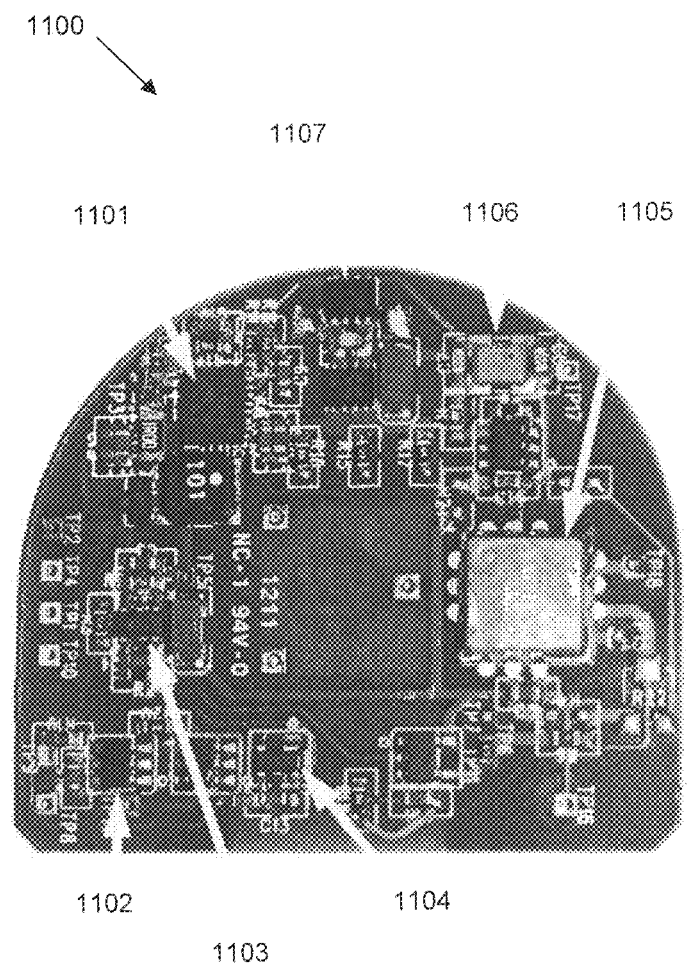
FIG. 11 is a representative bottom view of a RF power/data board, in accordance with some embodiments.

FIG. 11 shows the bottom view 1100 of a second flexible planar integrated circuit board PCB-B with embedded designed internal wiring, in accordance with some embodiments. PCB-B may be made of a material such as Kapton. The role of PCB-B is that of a wireless communication link on one hand and ability to receive electrical power coupled inductively to the SBNC on the other. Bottom view 1100 of PCB-B may include the following components: switching charger 1101, battery PCM 1102, regulator 1103, battery monitor 1104, RF transmitter 1105, testing circuitry 1106, and full-wave rectifier 1107.

Figure 12:
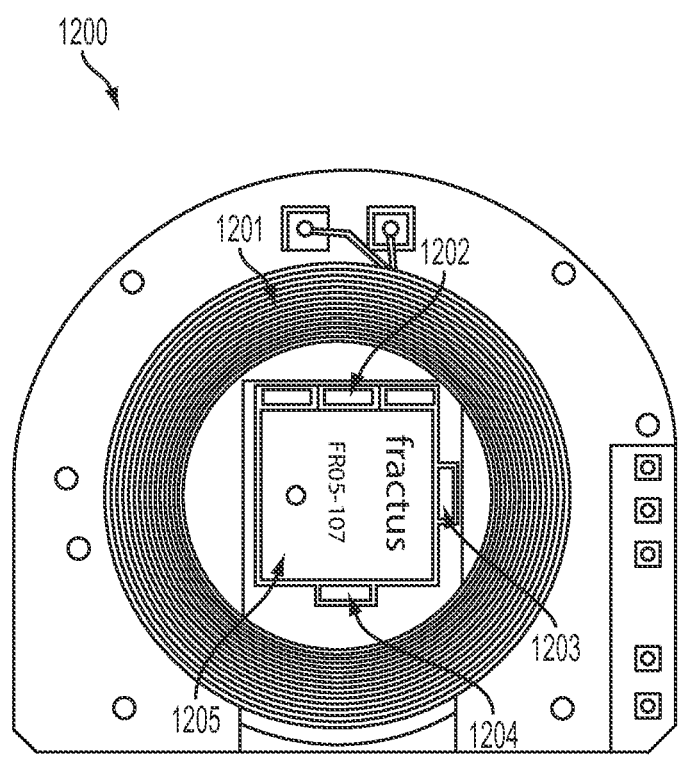
FIG. 12 is a representative top view of a RF power/data board, in accordance with some embodiments.

FIG. 12 shows the top view 1200 of circuit board PCB-B, in accordance with some embodiments. Top view of PCB-B may include the following components: RF power coil 1201, three charger indicators 1202, an infrared (IR) data vertical cavity surface emitting laser (VCSEL) 1203, battery low indicator 1204, and RF data antenna 1205.

The telemetry circuits embedded in PCB-B, designed to communicate wirelessly with electronics and systems outside the subject's head ("external world"), are composed of a radio/microwave (RF) frequency transmitter 1205 operating in a frequency and power range that is biomedically safe according to U.S. Food and Drug Administration regulations, communication-permissible according to U.S. Federal Communications Commission regulations, and capable of being secured. In one embodiment an RF link may be operated at a carrier frequency of 3.2 GHz using a FSK modulation scheme, providing up to 24 megabits per second (Mbps) of data transfer capability. Another alternative choice for RF signal modulation that is compatible with the design of the PCB-B is an ultra-wideband modulation scheme. Another alternative choice for RF technology could be an industry-standard wireless technology such as WiFi or Bluetooth. The transmitters are connected to dedicated antenna structures integrated within the PCB-B. RF transmission is intended for short distance telemetry or data transfer on the order of 1-10 meters to specifically configured RF electronic transceivers, with typical RF transmission power on the order of 1-10 mW. The RF antennas may be of a size suitable for 2-5 GHz radio transmission. This is made possible by the relatively large size of the SBNC unit, as smaller implantable devices lack the physical room to provide antenna structures ideally adapted for RF transmission.

The PCB-B also houses an infrared microcrystal semiconductor laser that may be a vertical cavity surface-emitting laser (VCSEL) 1203 operating near the 850 nm wavelength, in the infrared or near-infrared spectrum, where the skin of primates is relatively transparent. This enables an additional modality for very short distance wireless communication of approximately 10-100 cm from the subject, by transmitting laser light through the transparent window and through the user's skin to an optical receiving device positioned immediately on the other side of the skin boundary. The PCB-B may also include light-emitting diodes (LEDs) that may be used to show status of the device through the optical window, which may be useful for troubleshooting or for providing information outside of the telemetry transmission channel. Battery low indicator 1204 and charging indicators 1202 may be LEDs configured in this manner.

Receiving coil 1201 is for capturing RF power sent from a body-external unit for recharging the on-board battery, when such recharging is required. The receiving coil operates on the principle of inductive coupling, according to well-known principles of electromagnetic induction. Its time-varying flux may provide the DC electrical power for the battery through standard rectifier circuitry, while the RF frequency may be used as a timing reference ("clock") for either or both PCB-B and PCB-A in terms of their data management, mutual synchronization, and synchronization with electronics outside the subject's body.

In some embodiments, the electronic function, integration and spatial arrangement of the individual above listed components on the PCB-B provides connectivity matching with other functional elements in the SBNC such as the parallel interface plate (PIP), Ti-can feedthrough pin layout, electrical connectivity to PCB-A and the battery, while ensuring the stacking compatibility of the PCB-B as a geometrically planar, thin constituent layer for the overall nested arrangement of all the electrically functional units which compose the SBNC as already shown in the figures above.

In some embodiments, the RF receiving coil 1201 for capturing RF power may be used as an alternative to the standard RF antenna, and may have a higher bandwidth. This enables two-way communication with the microelectrode array (MEA) via the SBNC circuitry.

The physical assembly and fabrication of the SBNC and its final hermetic sealing by welding employ various physical device processing manufacturing tools and methods.

Figure 13:
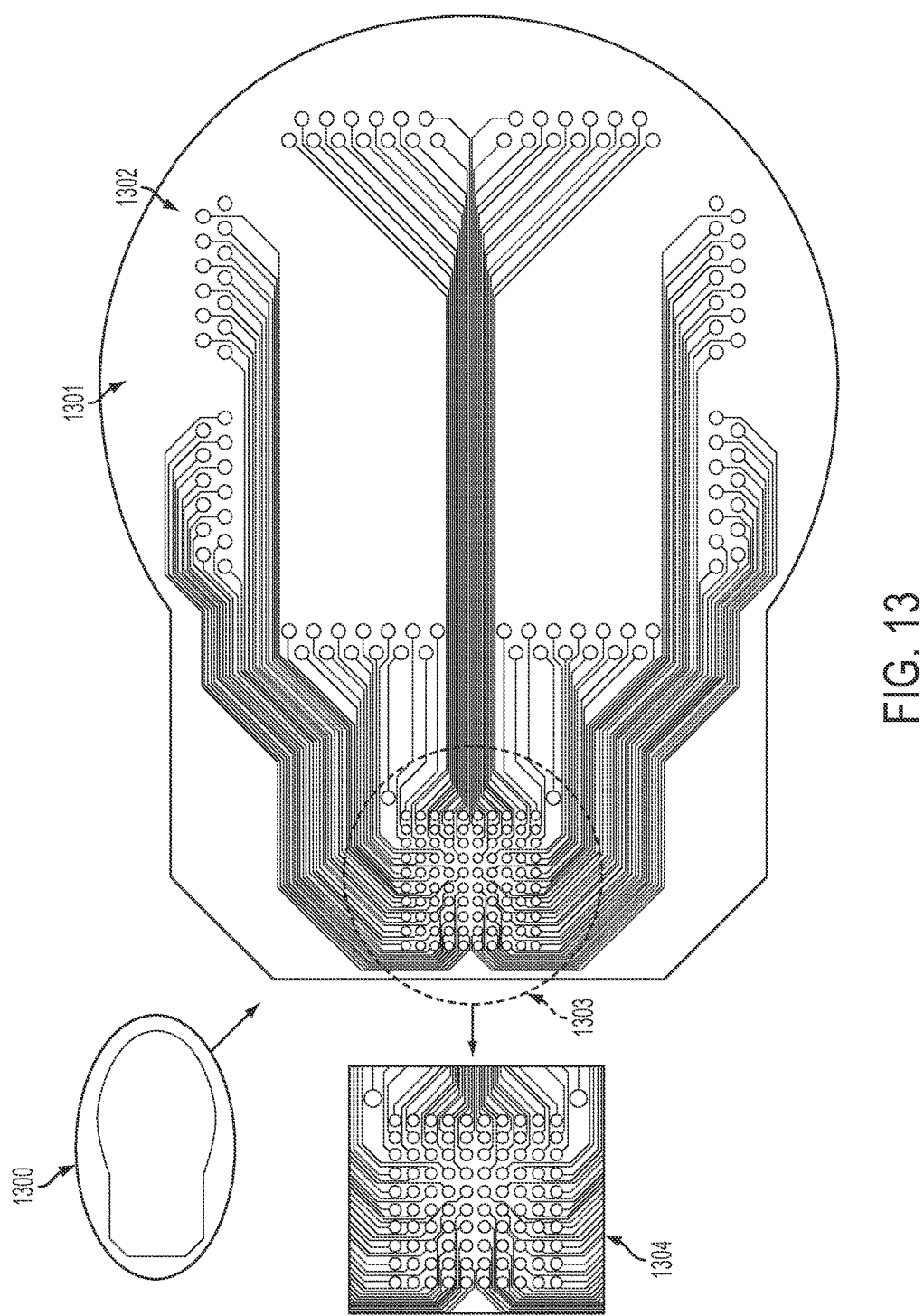
FIG. 13 is a representative diagram of an interface board for communication with a neural sensor, in accordance with some embodiments.

FIG. 13 is a representative diagram of an interface board for communication with a neural sensor, in accordance with some embodiments. Interface board 1300, also called a parallel interconnect plate (PIP), corresponds to plate 607 in FIG. 6. PIP 1300 has a substrate 1301 that may be made of Kapton. PIP substrate 1401 contains holes 1302 that connect to interface pins (not shown); these interface pins are connected beneath the PIP 1300 to a wire bundle that connects to a micro-electrode array (not shown). PIP testing substrate 1303 is shown in more detail at reference number 1304. All connections from holes 1302 are collected at testing substrate 1303 and passed to the preamplifier board, shown below.

Figure 14:
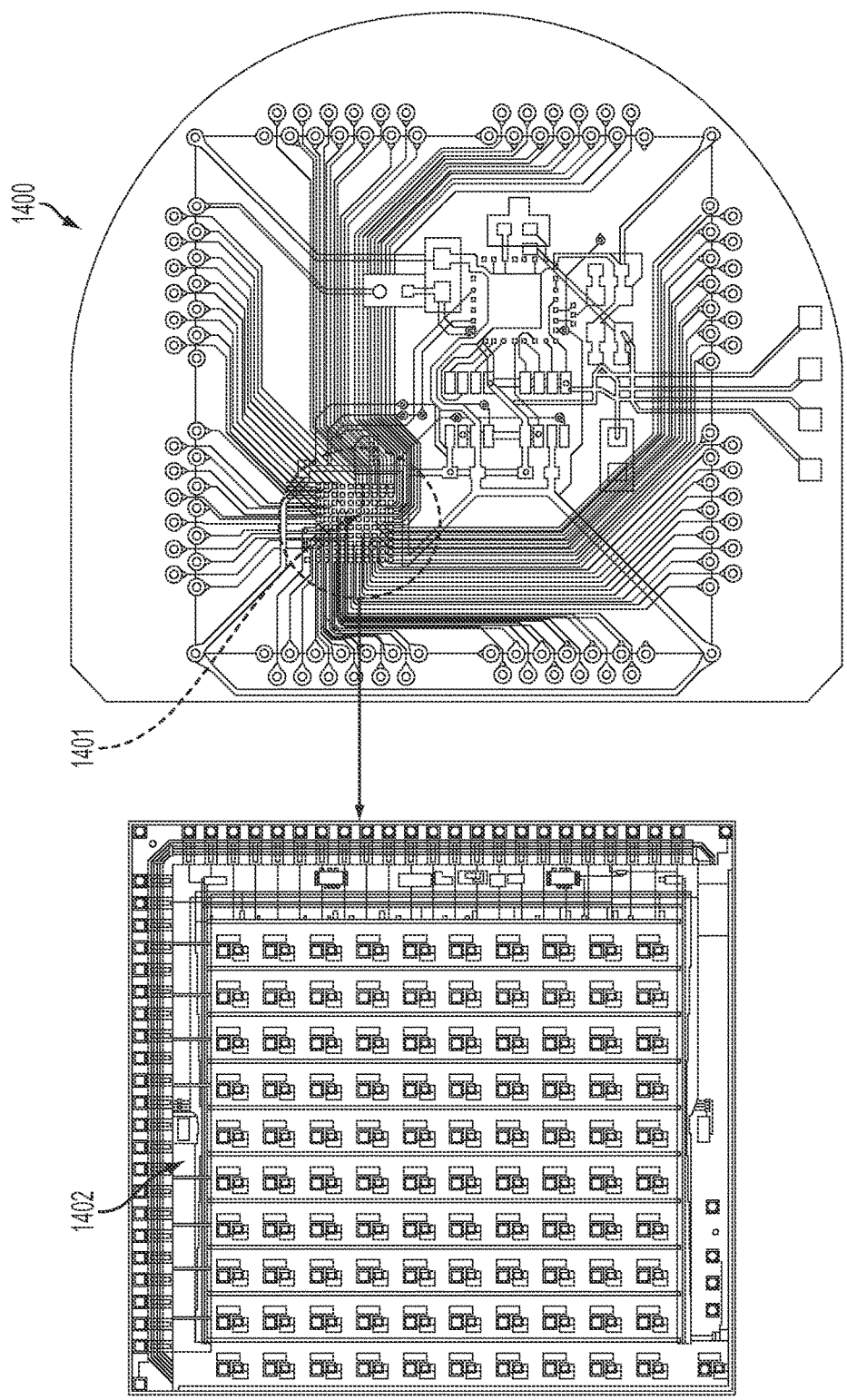
FIG. 14 is a representative diagram of a preamplifier board for communication with a neural sensor, in accordance with some embodiments and related to FIGS. 6 and 7.

FIG. 14 is a representative diagram of a preamplifier board for communication with a neural sensor, in accordance with some embodiments. Preamplifier board 1400 contains individual amplifier circuits 1402 arranged in an array 1401. One amplifier is provided for each electrode in the micro-electrode array. One hundred or more amplifiers may be provided. Although a specific number of amplifiers may be provided by preamplifier board 1400, the connections provided to the multi-electrode array may be multiplexed into a number of channels different from the number of amplifiers provided.

Both current stimulation and impedance spectroscopy may be incorporated into the 100-channel preamplifier chip, such that every channel can operate in three different modes: recording mode, current stimulation mode, and impedance spectroscopy mode. The determination of which channel is used in which mode is controlled by the commands sent wirelessly from the external unit. The following set of figures describes these in sequence.

Figure 15:
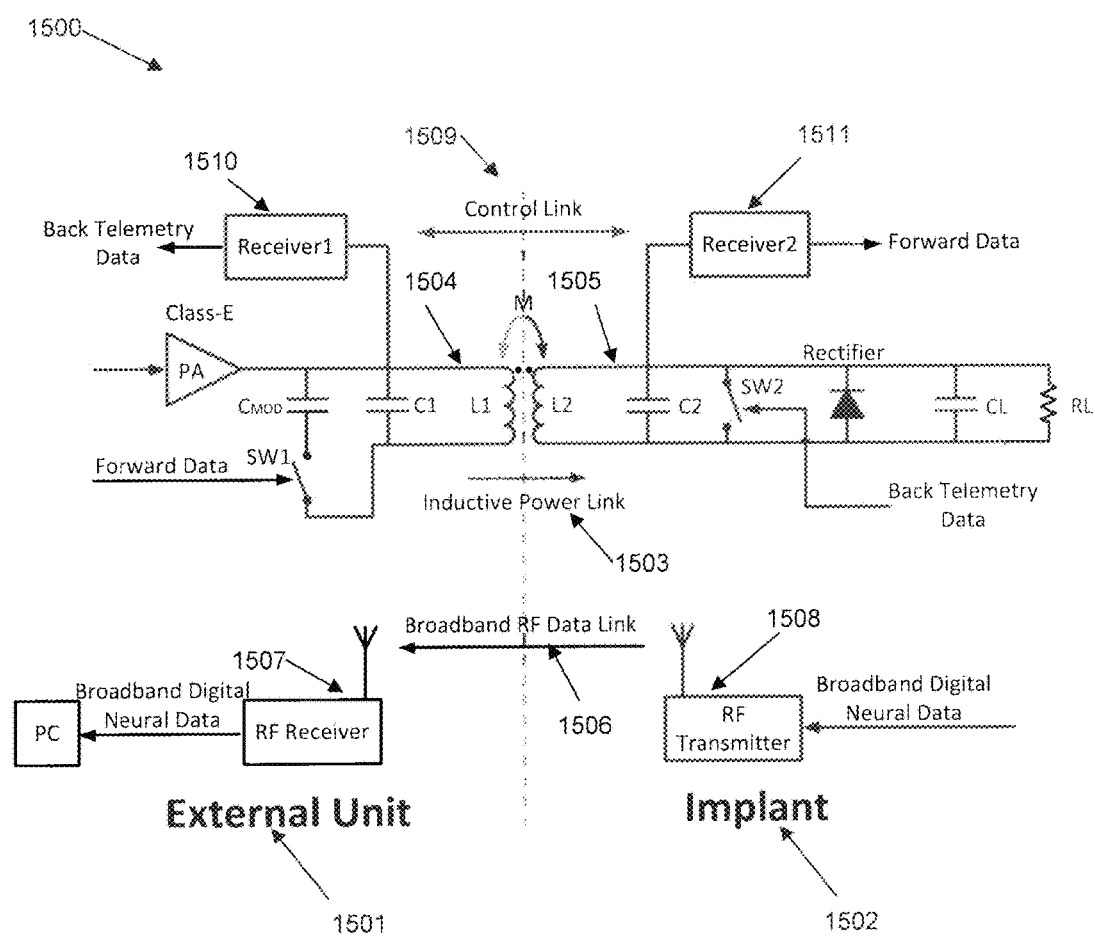
FIG. 15 depicts a block diagram of data transfer between devices in the system showing a forward data link for sending control commands, in accordance with some embodiments.

FIG. 15 depicts a block diagram of data transfer between devices in the system, showing a forward data link for sending control commands for current stimulation and impedance spectroscopy, according to some embodiments of the invention. For certain implantable devices that incorporate current stimulation, control signals may be needed for regulating the stimulating current to provide a flexible, safe, and robust stimulation protocol. Considering that the SBNC may be a fully implantable device, the command signal may be sent and received wirelessly. Therefore a wireless forward data link may be added. One way to implement the link is to take advantage of the power carrier/coil.

As shown in FIG. 15, a SBNC system 1500 may include an external unit 1601 that sits outside of the patient's body, and an implant 1502 that sits inside the patient's body. An SBNC may have three wireless links: an inductive power link 1503 between a power supply in the external unit 1504 and a power circuit 1505 in the implant; a broadband RF data link 1506, provided by an RF receiver 1507 on the external unit and an RF transmitter 1508 in the internal unit; and a control link 1509, provided by another RF receiver, Receiver 1 1510, in the external unit and another RF receiver, Receiver 2 1511, in the implant. In certain embodiments, additional wireless links may be added. The control link sending the control signal may be multiplexed onto the power link by using an amplitude-shift-keying (ASK) modulation scheme or other similar modulation scheme. The digital control data may be used to modulate the forward power carrier amplitude at a small scale, while an ASK receiver implemented in the implant may receive the power carrier change and extract the digital control signal, which may be decoded and used for control the parameters of the current stimulation and impedance spectroscopy (such as address, current amplitude, stimulation pulse frequency, pulse width, number pulses, etc.). In a preferred embodiment this ASK receiver may be implemented into the SBNC controller ASIC chip. An example of the format of the serial digital control signal is shown in Table 1 below:

this mode, the signal source 1801 is enabled and generates a biphasic current stimulation signal, whose profile and frequency are determined by the control data sent through the forward data link. An addressed recording electrode 1802 is connected to the signal source for current stimulation. The preamplifier input 1803 is grounded to protect the preamplifier from adverse situations and damage.

Figure 19:
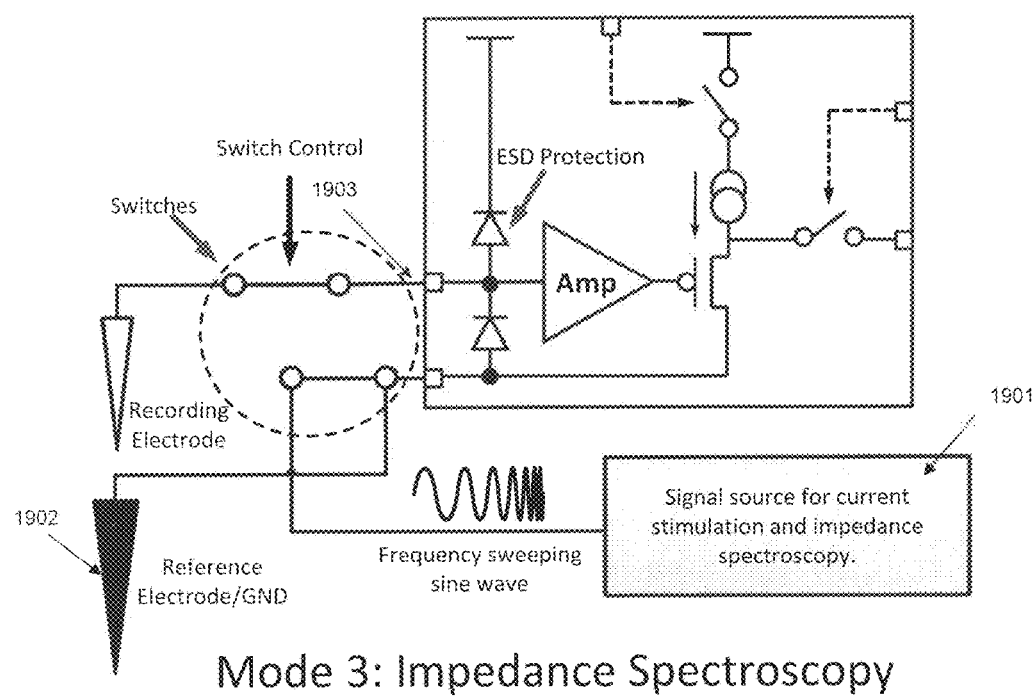
FIG. 19 is a schematic diagram of a preamplifier ASIC in impedance spectroscopy mode, in accordance with some embodiments.

FIG. 19 is a circuit diagram of a preamplifier ASIC in impedance spectroscopy mode, in accordance with some embodiments. In this mode the signal source 1901 is enabled and generates a variable frequency sine wave signal, which is connected to the global reference electrode 1902. The preamplifier input 1903 is connected to the recording electrode 1902. The inputs of all channels may thus "see" the variable frequency sine wave, recorded as waveforms on the receiver side. This allows for extraction of electrode impedances vs. frequencies, i.e. impedance spectroscopy for the electrodes. Since this feature may be implemented on the preamplifier chip of the implant, it may enable monitoring impedance changes of the electrodes after implantation. Two blocks that may be used to provide this function in some embodiments are a programmable current source for the stimulation and a variable frequency sine wave generator for impedance spectroscopy. These are represented in the figure as reference number 1901.

TABLE 1

An example of the current stimulation/impedance spectroscopy control data package
64 bits

| 8 bits | 1 bit | 2 bits | 8 bits | 10 bits | 10 bits | 12 bits | 4 bits | 8 bits |
|---|---|---|---|---|---|---|---|---|
| Start Synch | Discharge | Mode control (recording/ stimulation/ impedance spectroscopy) | Addressing (channel #) (1~100) | Positive stimulation current amplitude (10 uA~5 mA) and impedance spectroscopy frequency control | Negative stimulation current amplitude (10 uA~5 mA) | Stimulation pulse frequency (1 Hz~1 kHz) | # of stimulation pulses in each session. (1~16) | End synch |

Figure 16:
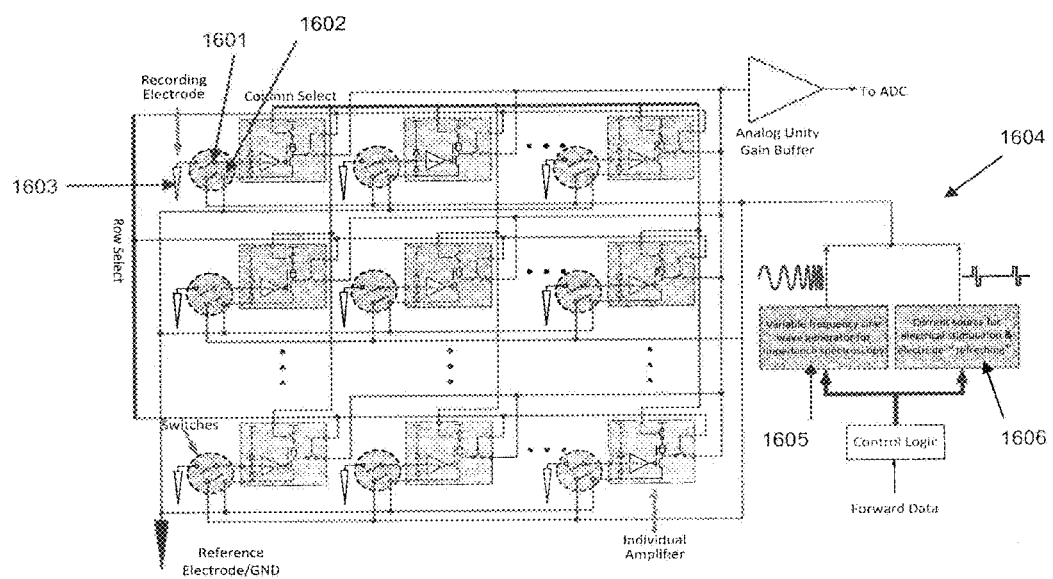
FIG. 16 is a circuit block diagram of a multi-channel preamplifier application-specific integrated circuit (ASIC), in accordance with some embodiments.

FIG. 16 depicts a circuit block diagram of a SBNC 100-channel preamplifier ASIC chip that implements recording, current stimulation, and impedance spectroscopy, according to some embodiments. Each channel may be switched into three different modes by switching its electrode to different circuitry on the ASIC. For each channel, there may be two analog switches implemented at the interface between the electrode and the ASIC. The switches 1601 and 1602, shown within the gray dashed circles, can connect a recording electrode 1603 to a preamplifier input, or to a current stimulation source, or a variable frequency sine wave generator of the impedance spectroscopy circuitry, allowing the channel to be in either a recording, or stimulation, or impedance spectroscopy mode.

Block diagram 1604 shows part of the control logic used for controlling the preamplifier ASIC. When modulating a forward data signal onto the electrical signal used as a stimulation source, a variable frequency sine wave generator 1605 may be used and its signal may be modulated onto the output of a current source 1606 for electrical stimulation and electrode refreshing.

Figure 17:
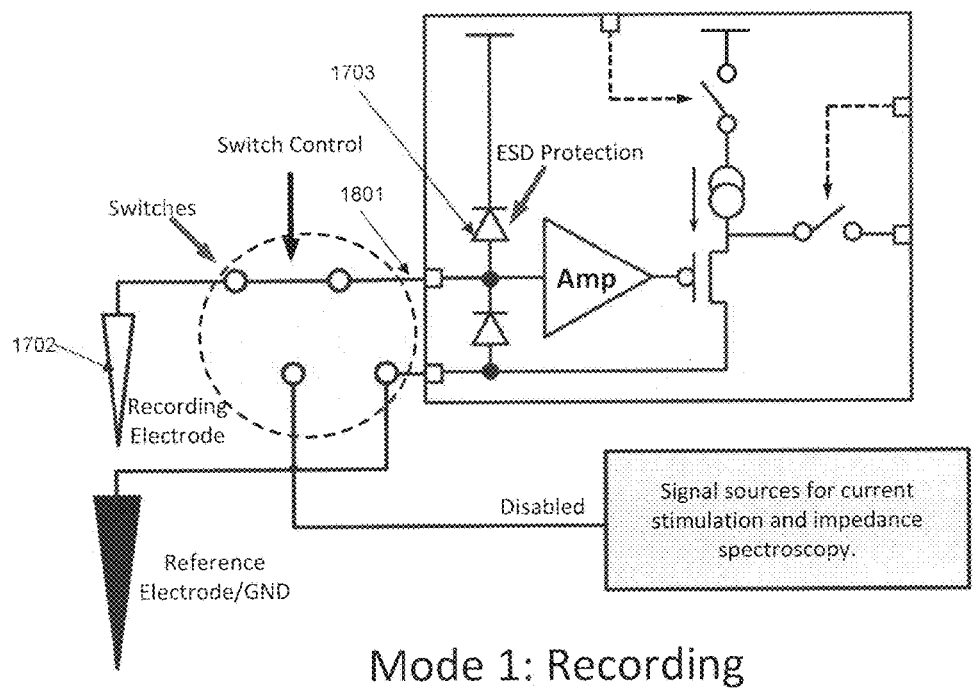
FIG. 17 is a schematic diagram of a preamplifier ASIC in recording mode, in accordance with some embodiments.

FIG. 17 is a circuit diagram of a preamplifier ASIC in recording mode, in accordance with some embodiments. In this mode, the preamplifier input 1701 is connected to the recording electrode 1702 and the signal source is disabled, such that the system may record neural signals for all recording electrodes. Diodes 1703 provide electrostatic discharge (ESD) protection.

Figure 18:
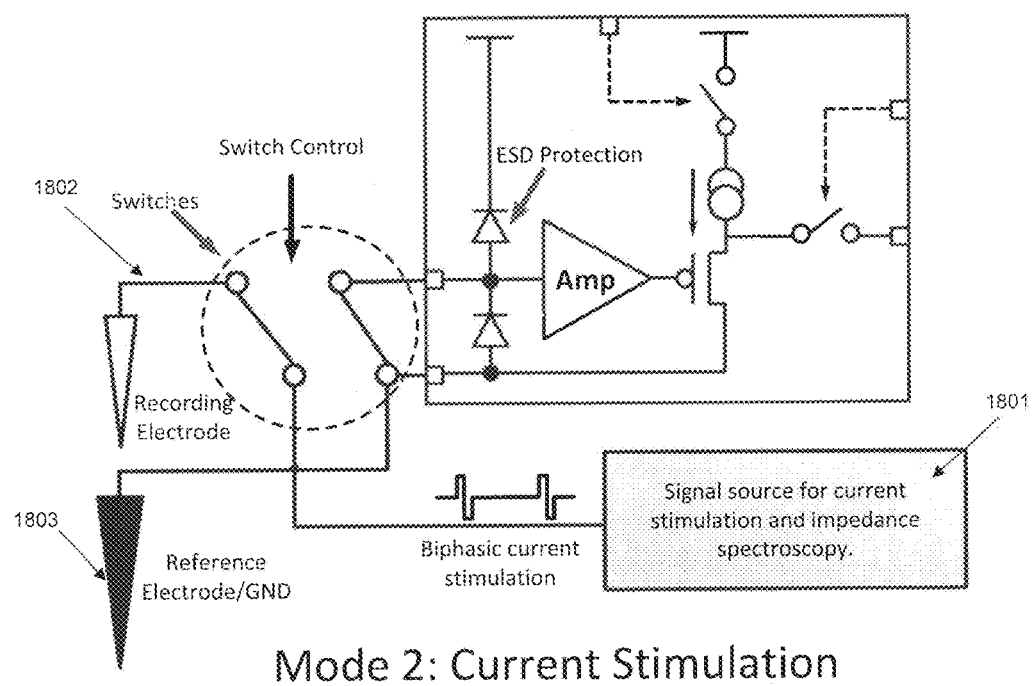
FIG. 18 is a schematic diagram of a preamplifier ASIC in stimulation mode, in accordance with some embodiments.
Figure 20:
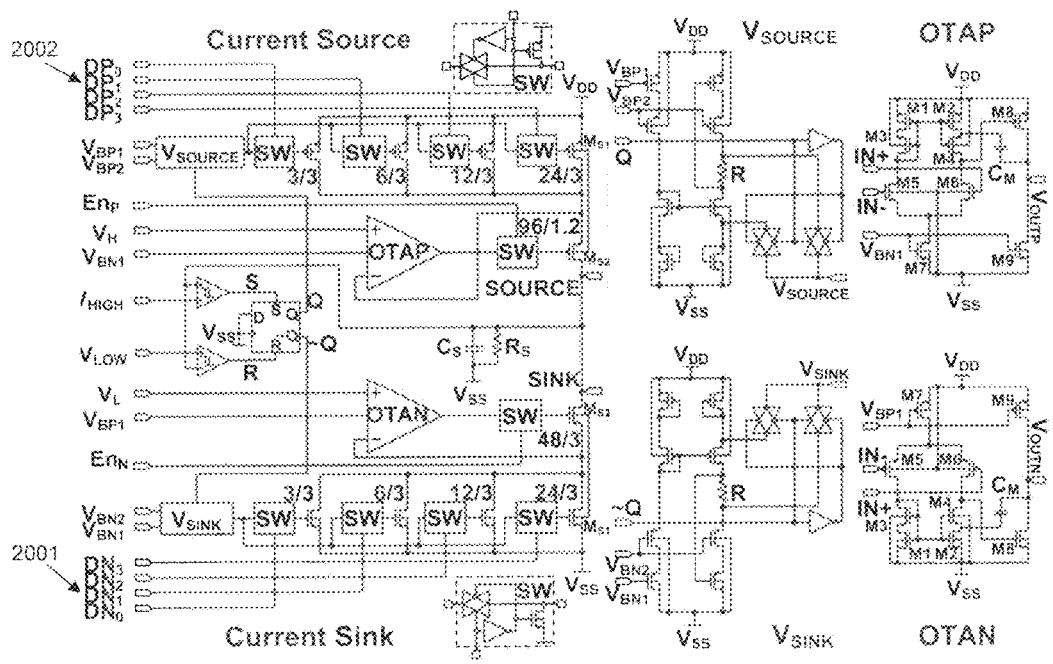
FIG. 20 is a schematic diagram of a programmable current source and sink unit, in accordance with some embodiments.

FIG. 18 is a circuit diagram of a preamplifier ASIC in stimulation mode, in accordance with some embodiments. In FIG. 20 shows an example of a programmable current source and sink unit for generating biphasic current stimulation signals in accordance with some embodiments. Such an embodiment may include a large voltage compliance digital programmable current source/sink unit. The programmable current source/sink may be controlled by digital bits DN0~DN3 2001 and DP0~DP3 2002, which are extracted from the serial control bits. The current source/sink also may have almost rail-to-rail compliance voltage, for providing a high output impedance for the current source/sink over the supply voltage range, therefore minimizing the load modulation effect of the electrodes and tissue interface, and providing fine-grained control over the stimulation current.

Figure 21:
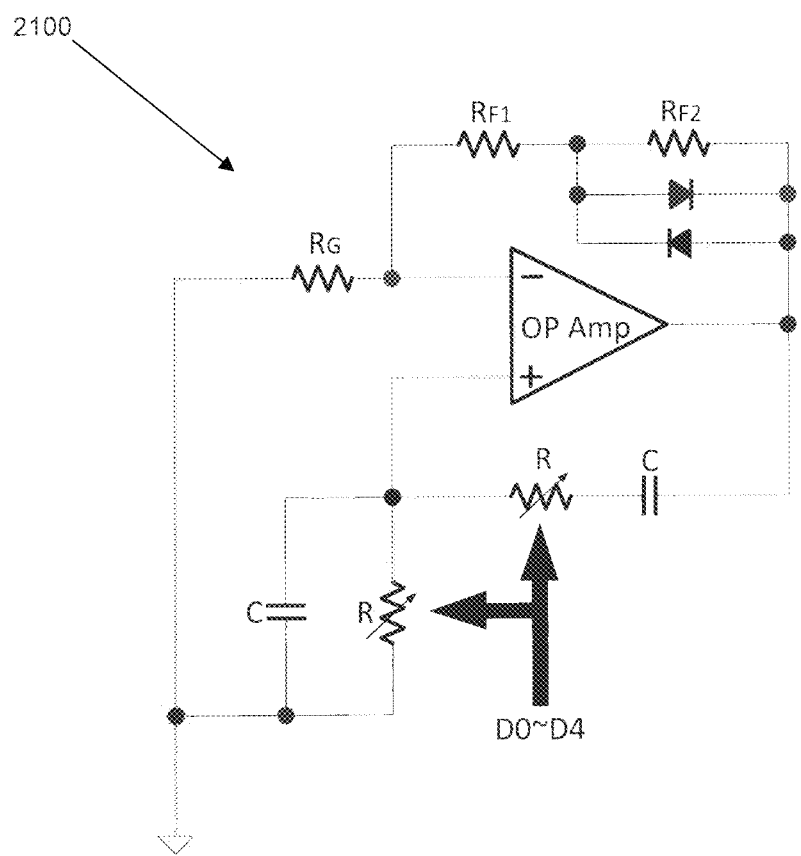
FIG. 21 is a schematic diagram of a variable frequency sine wave generator, in accordance with some embodiments.

FIG. 21 shows an example of a variable frequency sine wave generator 2100 for impedance spectroscopy in accordance with some embodiments. The specific scheme shown is a Wien Bridge Oscillator scheme, but other schemes may also be used. Since the output sine wave frequency is determined by 1/RC, by varying a resistance value R digitally through D0~D4, a sine wave may be generated with a frequency band covering the band of interest.

Figure 22:
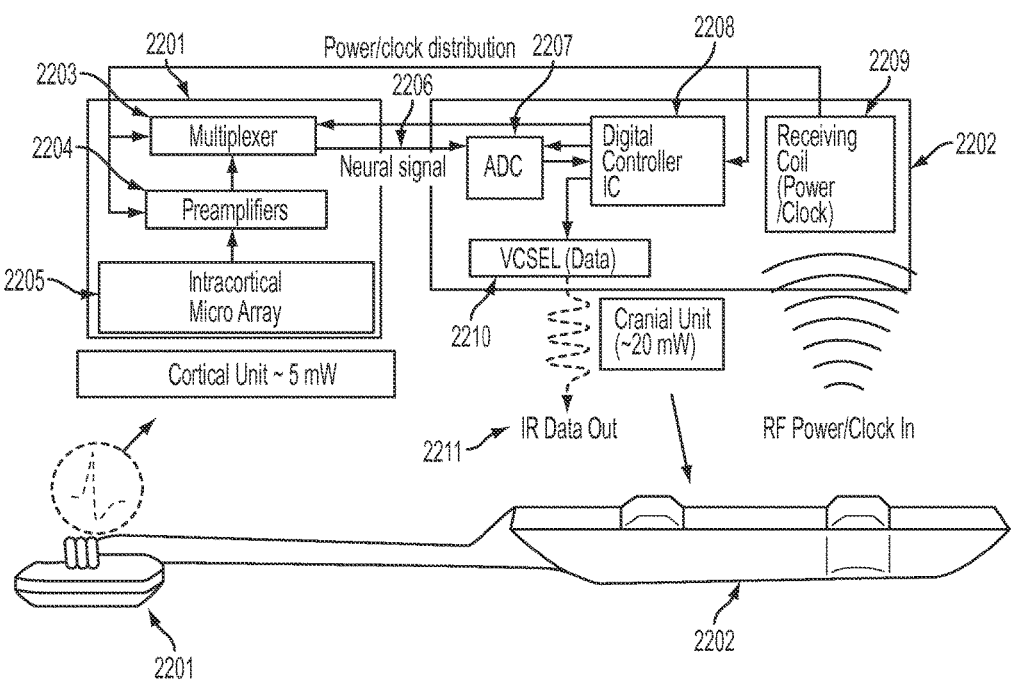
FIG. 22 is a block data transfer diagram of a cortical unit and a cranial unit, in accordance with some embodiments.

FIG. 22 is a block data transfer diagram of a cortical unit and a cranial unit, in accordance with some embodiments. Cortical unit 2201 contains intracortical microarray 2205, preamplifiers 2204, and multiplexer 2203. Cranial unit 2202 contains analog-to-digital converter (ADC) 2207, digital controller IC 2208, and receiving coil 2209. The cortical unit 2201 is referred to elsewhere in this application as a microelectrode array (MEA), and is implanted into the brain itself.

In some embodiments, cortical unit 2201 samples brain data, amplifies it using preamplifier 2204, multiplexes all brain signaling at multiplexer 2203, and sends an analog neural signal 2206 through an interface to a cranial module external to the cranium of the user. This neural signal is then processed into a digital signal at ADC 2207 in conjunction with IC 2208. Cranial unit 2202 is capable of wireless data transmission and reception via one or both of a VCSEL optical data interface providing infrared data out 2211 and a receiving coil 2209 for receiving RF signals. In some embodiments, receiving coil 2209 may be for receiving RF data; in some embodiments, receiving coil 2209 may also be for receiving RF power and clock inputs 2212.

Figure 23:
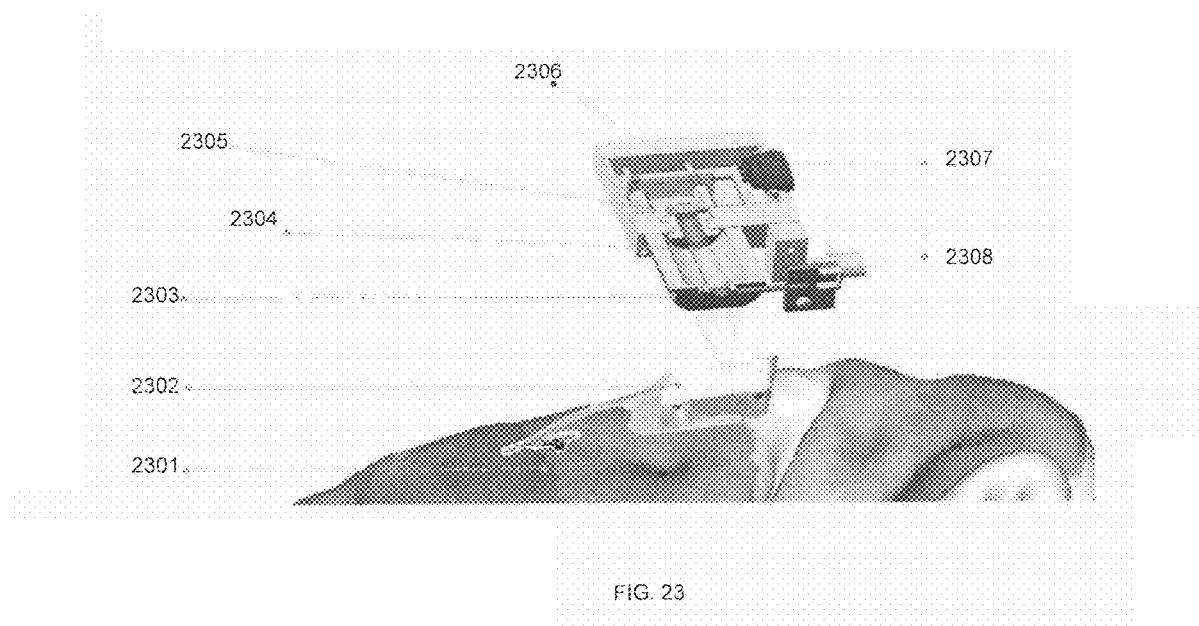
FIG. 23 is a representative diagram of an external interface device, in accordance with some embodiments.

FIG. 23 is a representative diagram of an external interface device, in accordance with some embodiments. Device 2306 is a "head-hugging" external cranial unit to be paired with the cranial unit 2302 of the previous figure, here labeled 2302 and implanted in brain 2301. External cranial unit 2306 contains an RF primary coil 2303 that serves as a power transmitter, a data transceiver, or both. External cranial unit 2306 also includes optical waveguide 2304, for use with receiving and transmitting data using the vertical-cavity surface-emitting laser (VCSEL) infrared connection. Photodiode and preamplifier circuit 2305 receive data from the optical waveguide 2304. Electrical and magnetic shielding is also provided by external cranial unit 2306. A DC power connection 2307 and RF drive input 2308 is provided for external cranial unit 2306 as well.

Overall, by using the method and circuitry that mentioned in previous paragraphs, a SBNC device may be built in such a way that incorporates recording, stimulation, and impedance spectroscopy capacities in a single implantable device.

In another aspect, the neural interface device includes an externally-mounted neural interface module that communicates through a wired connection to an implanted cranial module that collects and transmits data received from an electrode array implanted in the brain, and wirelessly to external devices. This system may be termed an External Brown Neural Card (E-BNC). The externally-mounted neural interface module is attached externally to a subject's head and mated onto a skull-mounted pedestal. The pedestal is a transcutaneous attachment device that is capable of attaching to and detaching from an E-BNC telemetry module. The pedestal in turn provides a pass-through port for wiring from below the subject's skin through the skull to an implanted intracortical or epicortical multielectrode array. The implanted array may be capable of data reception, transmission and recording from brain microcircuits and their electrical impulses wirelessly or via physical wires. A specific compact configuration is also disclosed which can be employed by animal and human subjects to access brain circuits using a lightweight, battery-powered, easily-detachable modular unit. In some embodiments, the device may have a profile of Φ31 mm×9 mm, including the mating pedestal.

In some embodiments, the device is capable of high-bandwidth wireless data transfer. The device may be capable of 100 channels for neural broadband data in recording and stimulation (from 0.1 Hz to 10 kHz), and may be scalable to hundreds of such independent neural data channels. 12-bit or 16-bit ADC resolution and 20-40 thousand samples per second per channel (kSps/Ch) may be provided for each channel. Radio-frequency (RF) wireless data telemetry may provide 24 Mbps data throughput, encoded using the Manchester FSK encoding or other encodings. RF output power may be in the range of 3 dBm. At one meter distance and using a 1.5 dBi antenna, measurable output power may be in the range of −40 dBm in some embodiments. Various wireless technologies may be used to provide this capability.

In some embodiments, the disclosed E-BNC provides the advantages of compact, wearable, wireless communications while being physically smaller than commercial neural recording systems that are cabled to external electronics. Examples of wired systems include those made by Black-Rock Cerebus Systems, Plexon Neurotechnology Research Systems, and Tucker-Davis Technologies' Multi-Channel Neurophysiology Workstation. Compared with wireless recording systems such as Triangle BioSystems' wireless recording system and Stanford's Hermes systems, the disclosed embodiments provide lighter weight and added performance through providing a larger number of broadband neural signal channels. Additionally, the disclosed embodiments may provide the added capability for in-situ impedance spectroscopy as a diagnostic method for the microelectrode array-brain tissue interface. Additionally, some embodiments may provide the capability to receive wireless commands for electrical microstimulation to the brain across the implanted microelectrode array, providing stimulation with a high degree of patterned spatial and temporal resolution.

The E-BNC system may employ a "screw-top" interface for mating the skull-mounted pedestal to an electronics assembly and battery array/battery pack. Other mechanisms may be used in addition to or in place of the screw threading mechanism, such as a tongue-and-groove mechanism, a magnetic seal, a spring-loaded latch mechanism, or others. The electronics assembly may include an amplifier printed circuit board (PCB) and wireless transmitter PCB, among other components. The battery array may be implemented as a series of batteries in a ring configuration, with a press-fit ball locking assembly configured to mate to the electronics assembly providing quick attachment/detachment. The locking assembly is configured with the electronics assembly oriented in the center and the battery pack surrounding the electronics assembly. Multiple battery packs may be attached together to the device to provide extended operational time. The battery system is safe without having to be hermetically sealed, as it is located outside of the body.

Figure 24:
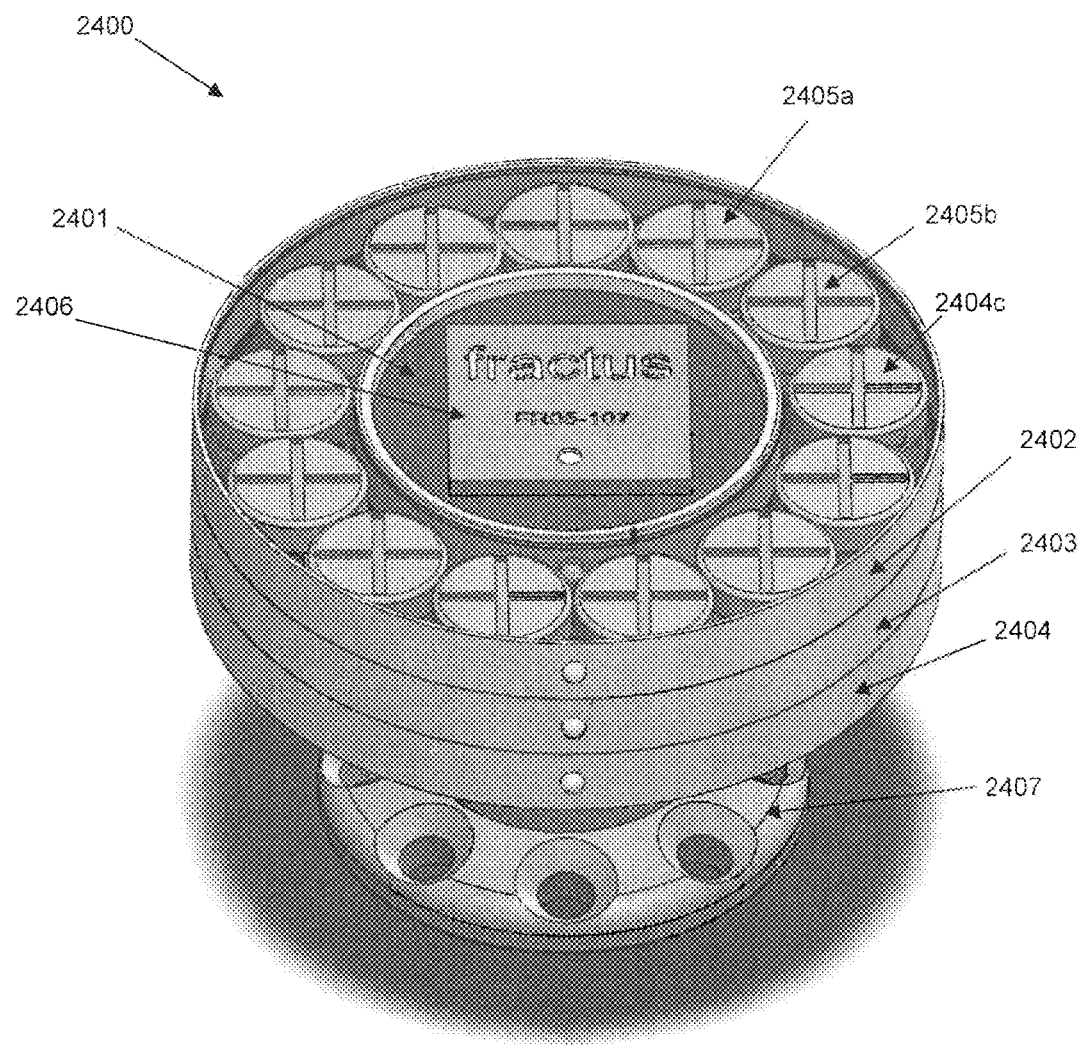
FIG. 24 is a perspective diagram of an externally-mounted E-BNC module, in accordance with some embodiments.

FIG. 24 is a perspective diagram of an externally-mounted E-BNC module, in accordance with some embodiments. Externally-mounted neural interface 2400 is shown with pedestal 2407 and battery packs 2402, 2403, 2404. Each battery pack or battery array includes multiple batteries 2405a, 2405b, 2405c and is independently removable from device core 2401. A cylindrical section located within the inner circumference of battery pack 2402, shows the top face of device core 2401. A RF antenna 2406 is visible. The bottom of device core 2401 is mated to pedestal 2407, as will be shown hereinbelow.

Figure 25:
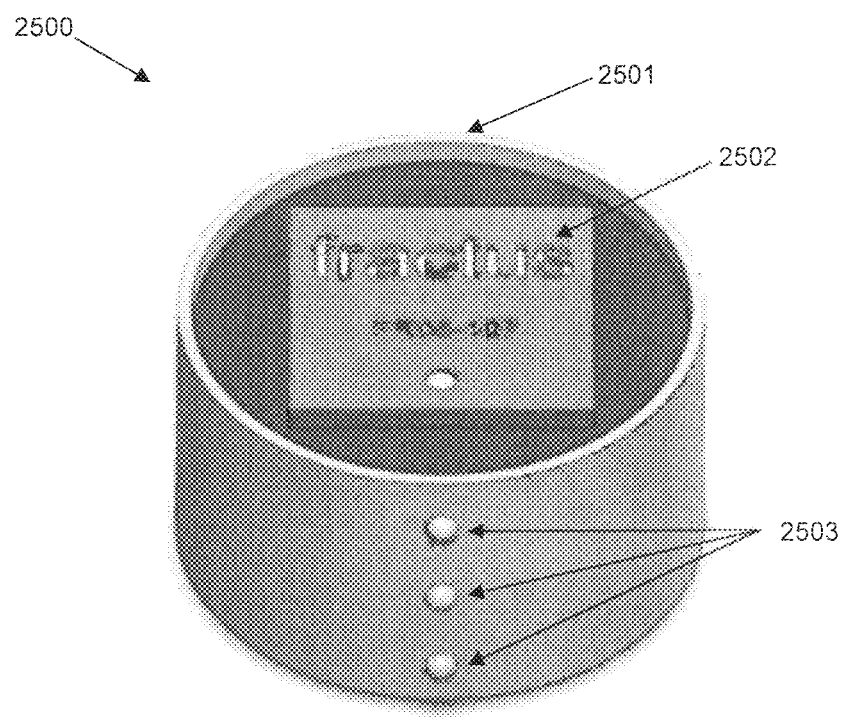
FIG. 25 is a perspective diagram of an externally-mounted E-BNC module without batteries, in accordance with some embodiments.

FIG. 25 is a perspective diagram of an externally-mounted E-BNC module without batteries, in accordance with some embodiments. Device core 2501 is shown unmounted from its pedestal and separated from its batteries. The electronic components discussed in the previously-described implantable embodiment may be contained within device core A. This has the advantage of being readily accessible without surgically reopening the body, allowing for a user to obtain upgraded hardware and electronics as needed. Device core 2501 is also separable from its pedestal. Three rows of attachment ball locks 2503 are shown for securing battery arrays to the exterior of device core 2501; in some embodiments, these locks may be used as electrical contacts. The ball locks provide a quick-release mechanism for the battery arrays. A RF antenna 2502 is visible.

Figure 26:
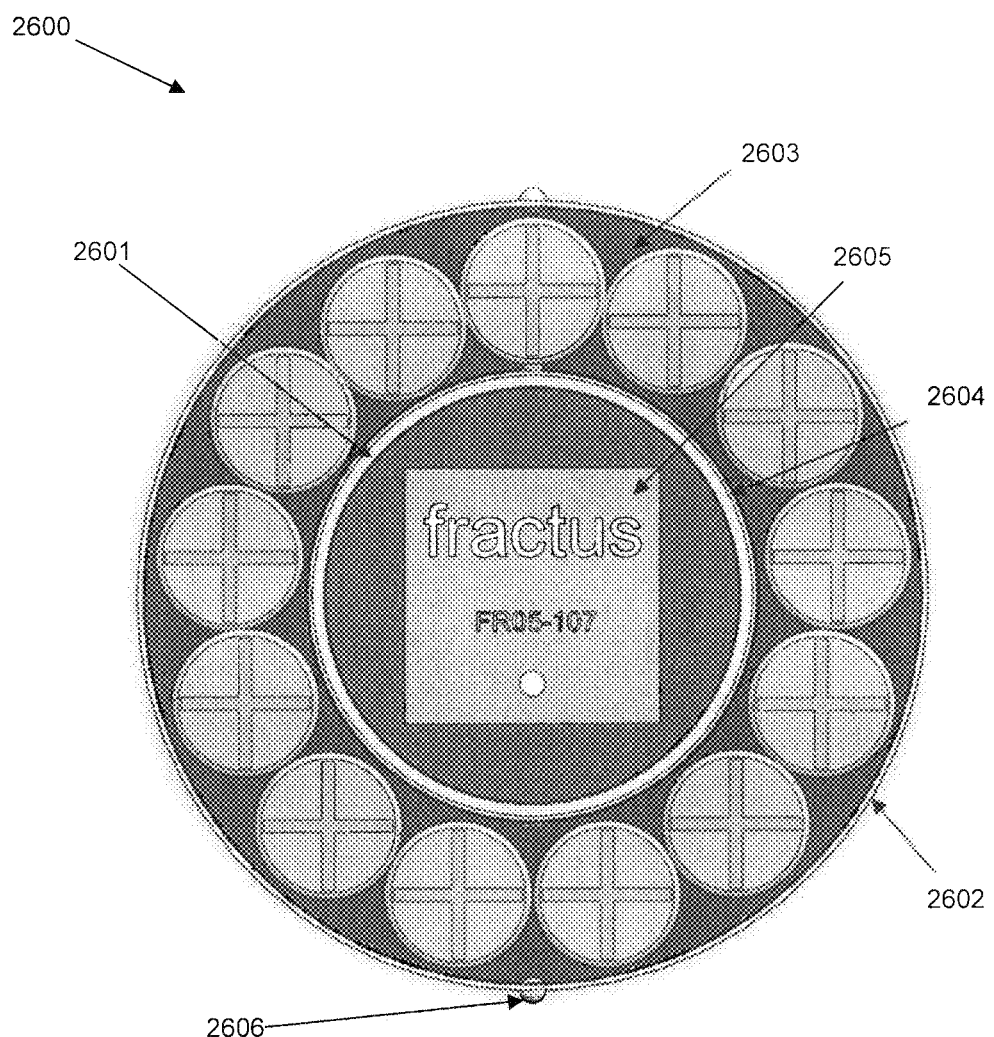
FIG. 26 is a top view of an externally-mounted E-BNC module, in accordance with some embodiments.

FIG. 26 is a top view of an externally-mounted E-BNC module, in accordance with some embodiments. In some embodiments, the external circumference 2602 of battery packs 2603 may be 31 mm, and the inner circumference 2604 of the battery packs may be 17.3 mm. Device core 2601 is contained within the inner circumference. Ball lock 2606 is shown from above for securing battery pack 2602. In some embodiments, RF antenna 2605 is positioned at the top of device core 2601 such that it is able to transmit data wirelessly to a nearby computer, such as a laptop connected via Bluetooth or WiFi technology.

Figure 27:
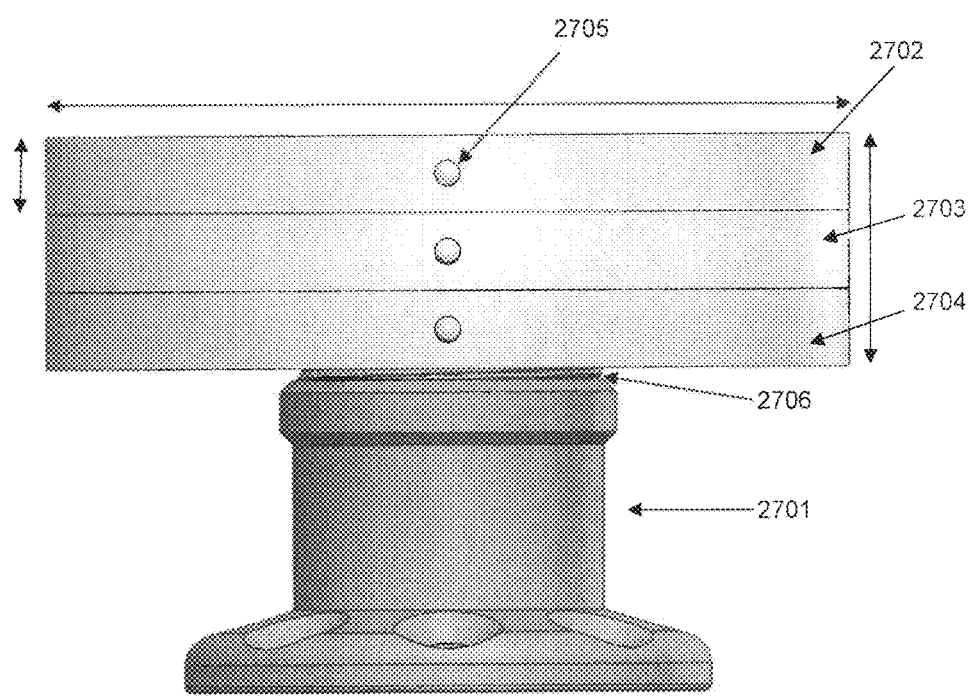
FIG. 27 is a side view of an externally-mounted E-BNC module, in accordance with some embodiments.

FIG. 27 is a side view of an externally-mounted E-BNC module, in accordance with some embodiments. In side view, the device core is not visible. Instead, the side view is dominated by three battery arrays in profile 2702, 2703, 2704, and pedestal 2701. pedestal C may be one or more pieces of machined biocompatible metal, or some other biocompatible material. The pedestal may be built to securely attach to the skull of the user using screws through screw holes 2705. As well, the pedestal is equipped with threading 2706 to allow device core A to be screwed onto its top. Other mechanisms may be used in addition to or in place of the screw threading mechanism, such as a tongue-and-groove mechanism, a magnetic seal, a spring-loaded latch mechanism, or others. The pedestal may be hollow, and the interior of the pedestal may house a wire bundle connecting the device core with an implanted micro-electrode array in direct contact with the brain and/or central nervous system. Biocompatibility of the pedestal housing allows the pedestal to be surgically implanted percutaneously with a reduced risk of infection or autoimmune rejection.

Figure 28:
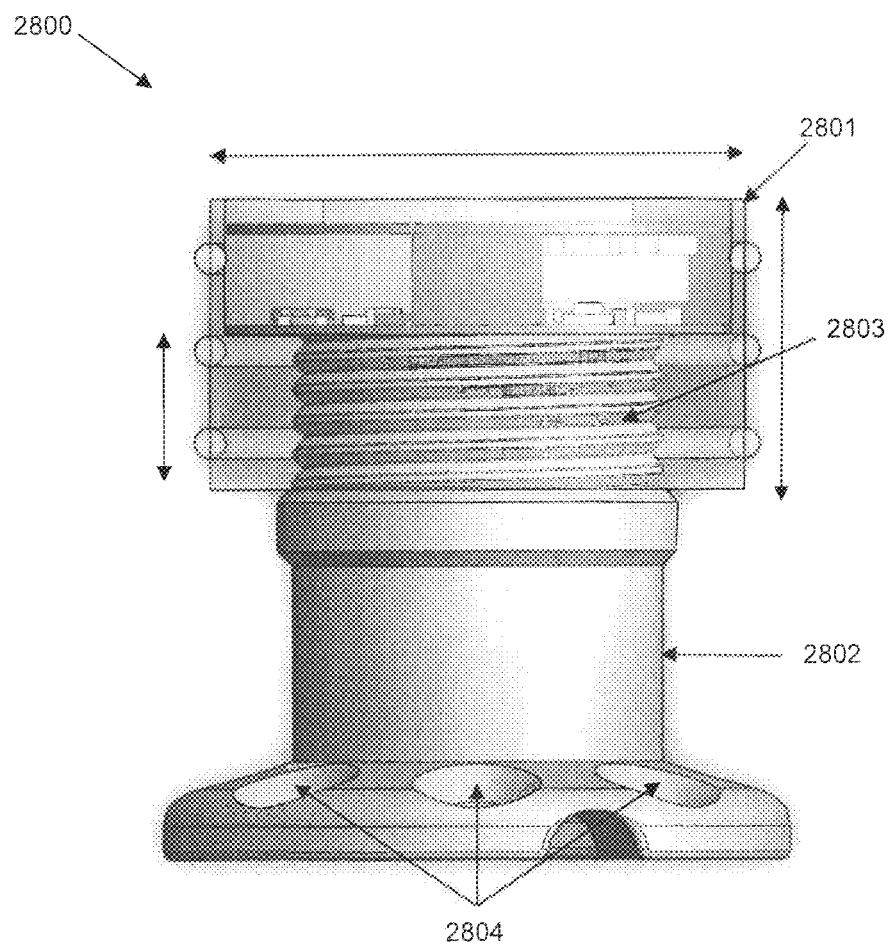
FIG. 28 is a cutaway view of an externally-mounted E-BNC module without batteries, in accordance with some embodiments.

FIG. 28 is a cutaway view of an externally-mounted E-BNC module without batteries, in accordance with some embodiments. In the cutaway, device core 2801 and pedestal 2802 are shown. The bottom of pedestal 2802 is fastened to the cranium or skull using screws via screw holes 2804 beneath the skin of a user, while the top of the pedestal is capped by device core 2801. Device core 2801 has a screw mating assembly to be able to be threaded onto the top of pedestal 2802. Rough dimensions of the device are given in the figure as 17.3 mm in diameter and 9 mm in height, with a 5 mm pitch between battery sites. In some embodiments, three battery sites are provided; in alternate embodiments, more or fewer battery sites could be contemplated.

Figure 29:
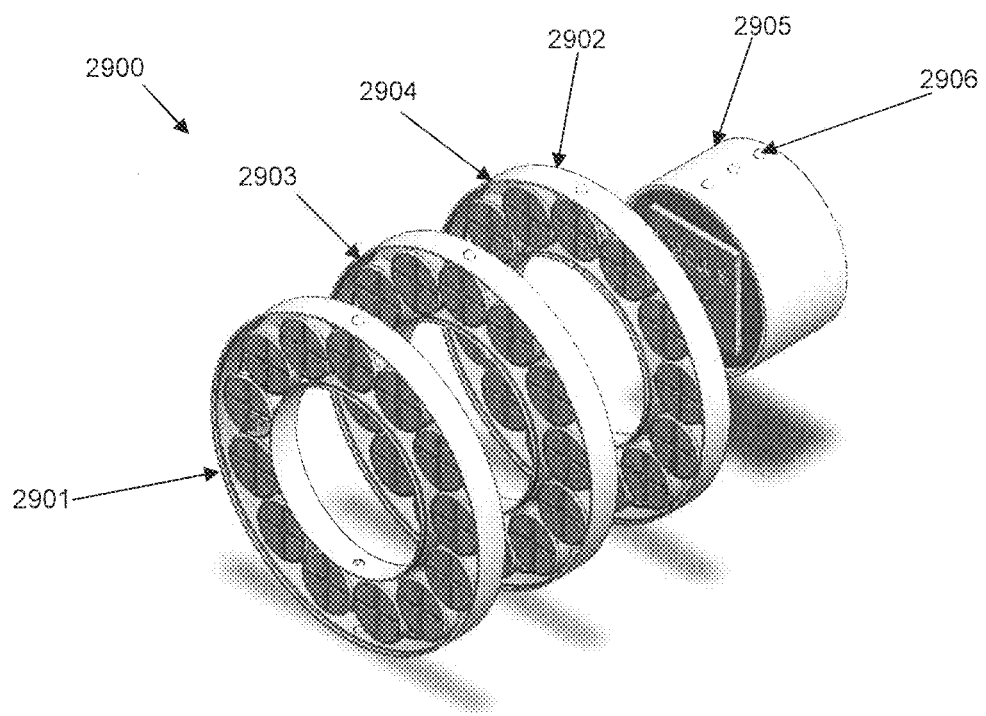
FIG. 29 is an exploded perspective diagram of an externally-mounted E-BNC module without batteries, in accordance with some embodiments.

FIG. 29 is an exploded perspective diagram of an externally-mounted E-BNC module without batteries, in accordance with some embodiments. Device core 2900 is shown to contain two circuit boards, wireless transceiver board 2901 and amplifier board 2902. Pedestal 2903 is shown from a perspective top view, and provides screw threads for mating with device core 2900. Ball locks 2906 are shown on the side of pedestal 2903. In some embodiments, device core 2900 may also contain a circuit suitable for charging a battery.

In some embodiments, the amplifier board 2902 includes the amplifier circuit to be connected with the external microelectrode array, and may contain analogs of all or substantially all of the components found on PCB-A of the present disclosure, as described below.

The bottom side of amplifier board 2902 has a plurality of metal pads, equal in number to the number of electrodes in the electrode array, that connect to the inputs of each amplifier. An anisotropic polymer connector that only conducts in the vertical direction and that is open in the horizontal direction may be used to connect metal pads to mating metal pads on the surface of the metal pedestal. The polymer connector provides a low-resistive electrical path. Neural signals travel from the implanted cortical electrode array through a multi-wire bundle and to metal pads on the pedestal. The signals then pass through the polymer connector and eventually arrive at the metal pads of amplifier board 2902. In some embodiments, a different number of channels or implanted electrodes may be provided, in which case the number of the wires used to carry the neural signals may vary.

The top side of amplifier board 2902 may include a multi-channel preamplifier ASIC 2907, controller ASIC, two ADCs, and a clock source. The top side of amplifier board 2901 amplifies and digitizes neural signals received from the metal pads. The digitized signals from each channel are multiplexed and packaged into a signal serial bit stream by a controller ASIC, which along with the power supply and the ground signals may then be fed into wireless transceiver board 2901 through a miniature spring-loaded 3-pin connector.

Wireless transceiver board 2901 includes the RF antenna 2905 and may contain analogs of all or substantially all of the components found on PCB-B of the present disclosure, including an internal coin battery, a battery PCM, a battery monitor, and a transmitter VCO. Wireless transceiver board 2901 integrates a voltage controlled oscillator and a miniature antenna capable of broadcasting the 3.2/3.8 GHz Frequency-Shift-Keying modulated digital neural signals. The wireless data may be received by a custom design receiver unit, similar to what has been used for the SBNC device, at a distance of several meters.

Figure 30:
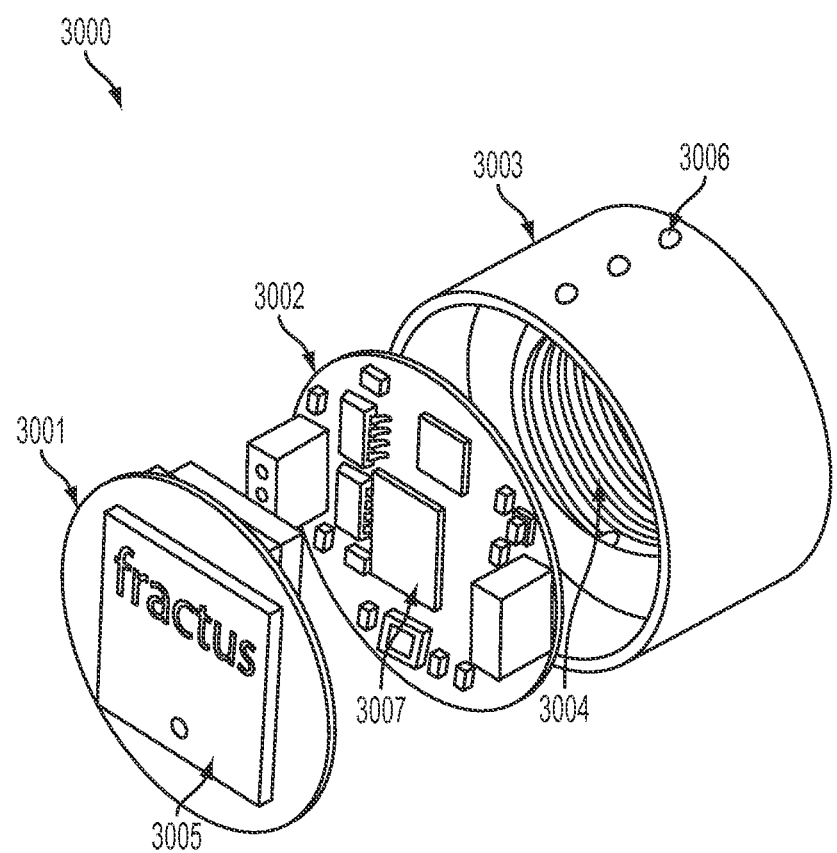
FIG. 30 is an exploded perspective diagram of an externally-mounted E-BNC module with batteries, in accordance with some embodiments.

FIG. 30 is an exploded perspective diagram of an externally-mounted E-BNC module with batteries, in accordance with some embodiments. A device core 3005 is shown together with multiple battery arrays 3001, 3003, 3004. These battery arrays can supply the system with enough power to run continuously for 15 hours. In some embodiments, power consumption for the system, including RF antenna and signal processing boards, may be in the 27 mA range. Multiple packs may be connected to device core 3005. Power packs may be added by pressing a pack down onto the central device core from the top onto ball locks 3006. The design specifically allows for the top pack to be removed while the bottom pack is still attached and providing power, so that more packs may be used to extend running time. In alternative embodiments, more than three battery packs may be attached.

Shown on the side of battery arrays 3001, 3003, 3004 are press-fit ball plunger locking mechanisms 3002. The ball plungers are mechanically coupled to locking components (not shown) located on the interior of each battery array and in contact with ball locks on the exterior of device core 3005. Locking mechanisms 3002 are configured to require a user to depress them with a set detent force, upon which a spring-loaded mechanism will result in the locking components on the interior of the battery arrays to retract, freeing the individual battery array. Two ball locks are located in a diametrically-opposed configuration, enabling a user to depress both locks using a thumb and finger. Other locking mechanisms can be contemplated, including a spring-loaded latch and a magnetic latch, for securely attaching the battery arrays. The ring shape of the battery arrays provides additional security.

Figure 31:
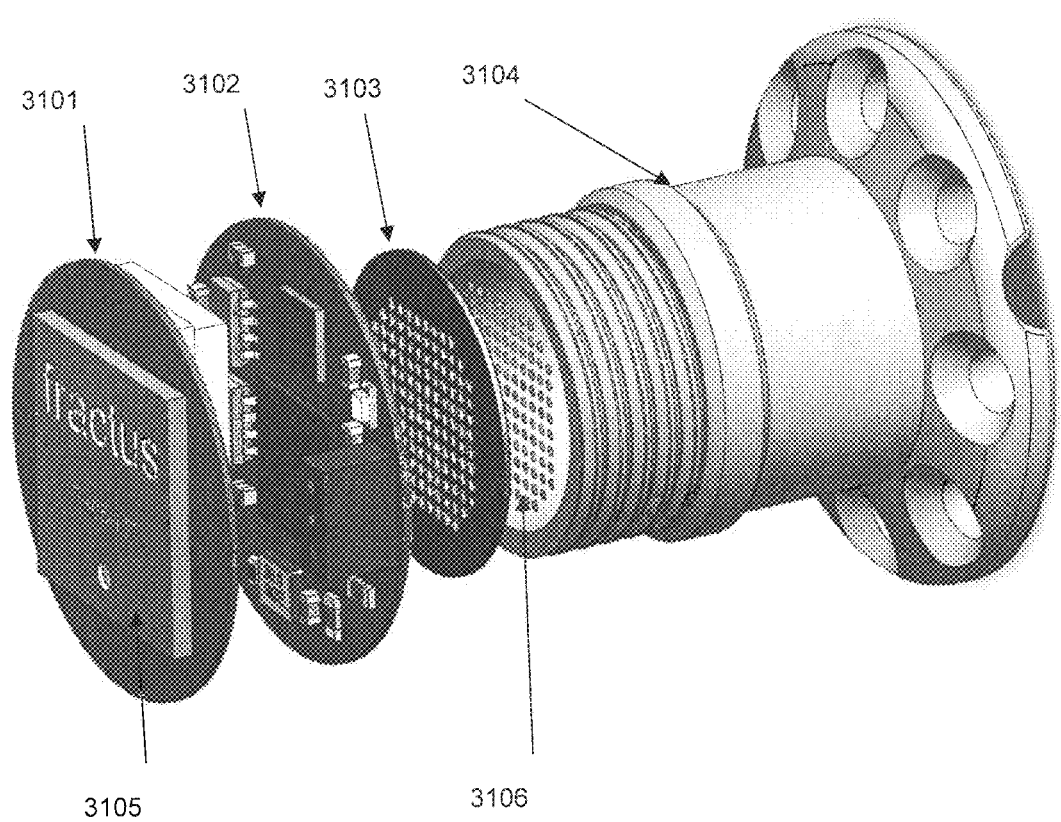
FIG. 31 is a top view exploded perspective diagram of an externally-mounted E-BNC module without case, in accordance with some embodiments.

FIG. 31 is a top view exploded perspective diagram of an externally-mounted E-BNC module without case, in accordance with some embodiments. Wireless transceiver board 3101, amplifier board 3102, interconnect board 3103 and pedestal 3104 are shown from the top. Wireless antenna 3105 is visible on the top of wireless transceiver board 3103.

Interconnect board 3103 is a polymer connector like that disclosed above. The pads of the polymer connector are designed to mate with pads on the exterior top of the pedestal, which in turn feed through to a wirebundle on the interior of the pedestal and through to the implanted microelectrode array.

Figure 32:
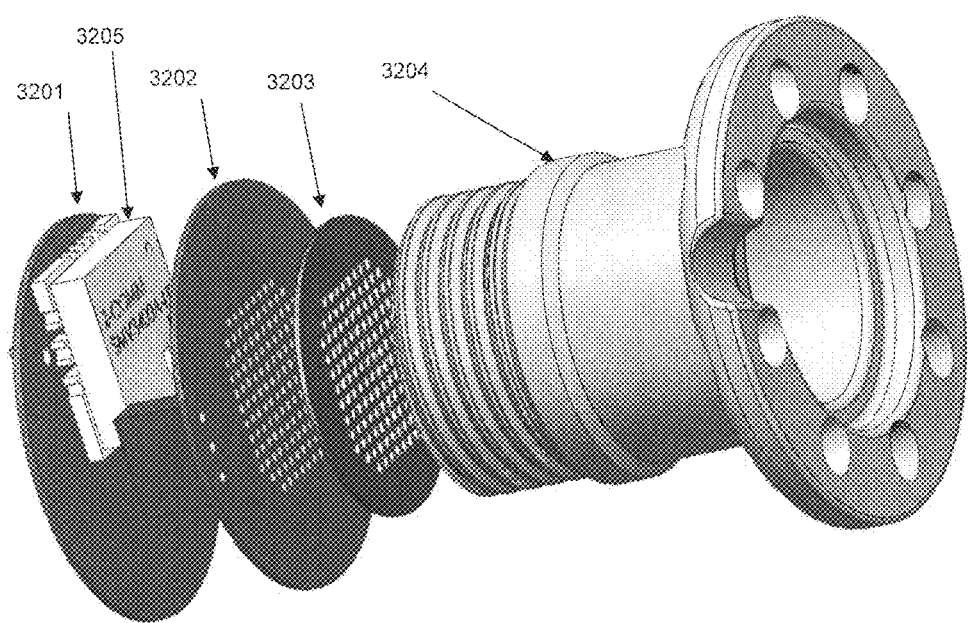
FIG. 32 is a bottom view exploded perspective diagram of an externally-mounted E-BNC module without case, in accordance with some embodiments.

FIG. 32 is a bottom view exploded perspective diagram of an externally-mounted E-BNC module without case, in accordance with some embodiments. Wireless transceiver board 3201, amplifier board 3202, interconnect board 3203 and pedestal 3204 are shown from the bottom. The bottom of the pedestal is hollow. The bottom of the amplifier board 3202 is shown to have pads that mate with those of the interconnect board 3203. Wireless transceiver chip 3205, which communicates with wireless antenna chip 3105, is visible on the bottom of the RF board.

Figure 33:
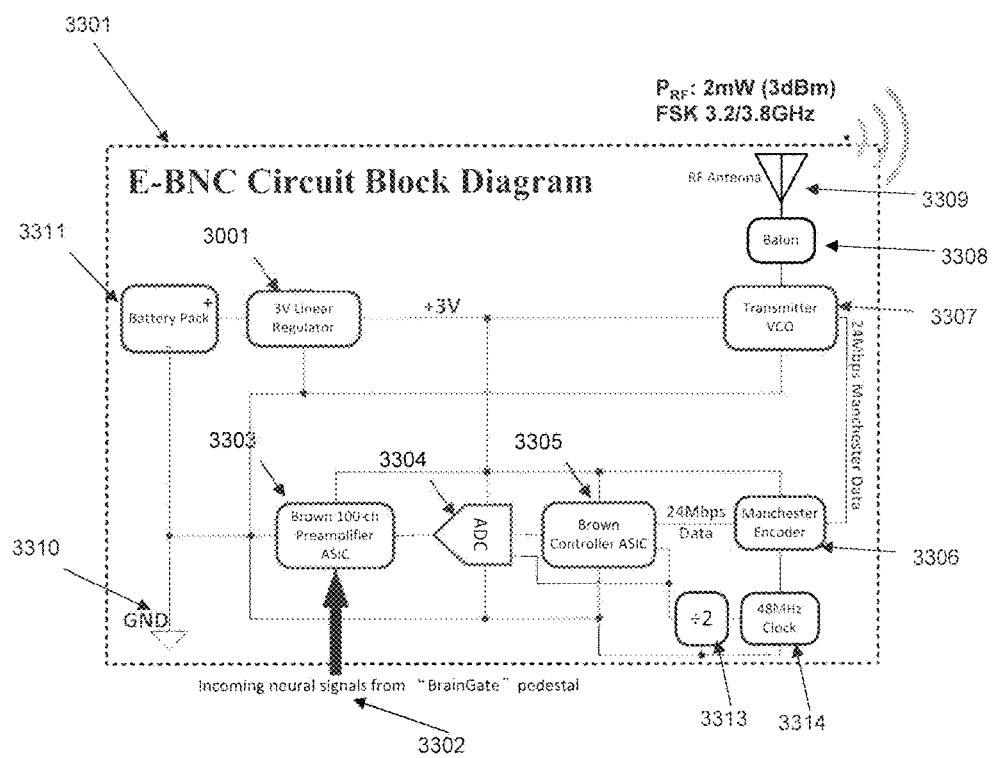
FIG. 33 is a circuit block diagram for an externally-mounted E-BNC RF power/data board and preamplifier board, in accordance with some embodiments.

FIG. 33 is a circuit block diagram for an externally-mounted E-BNC RF power/data board and preamplifier board, in accordance with some embodiments. Circuit diagram 3301 is representative of all necessary circuit boards and components in an E-BNC. At the bottom of diagram 3301 is arrow 3302, representing incoming neural signals from the implanted microelectrode array. This feeds in turn into: preamplifier ASIC 3303, ADC 3304, controller ASIC 3305, and Manchester encoder 3306. Other encoders may be provided. Once the received data has been encoded it is sent to transmitter VCO 3307, which sends it to balun 3308, which transmits the signal via radio frequency antenna 3309. The power of the signal is 2 milliwatts at one meter (3 dBm), and the signal is 3.2/3.8 GHz FSK. Other components necessary for functioning are provided, such as ground 3310, battery 3311, linear regulator 3312, clock divider 3313, and clock 3314.

Figure 34:
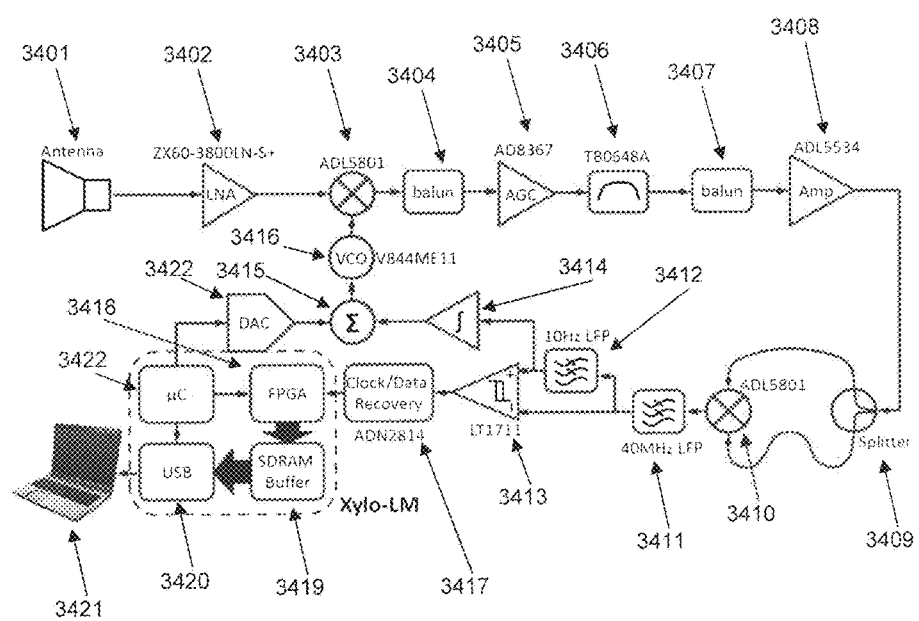
FIG. 34 is a radio block diagram for a receiving apparatus for wirelessly communicating with a wireless E-BNC, in accordance with some embodiments.
Figure 35:
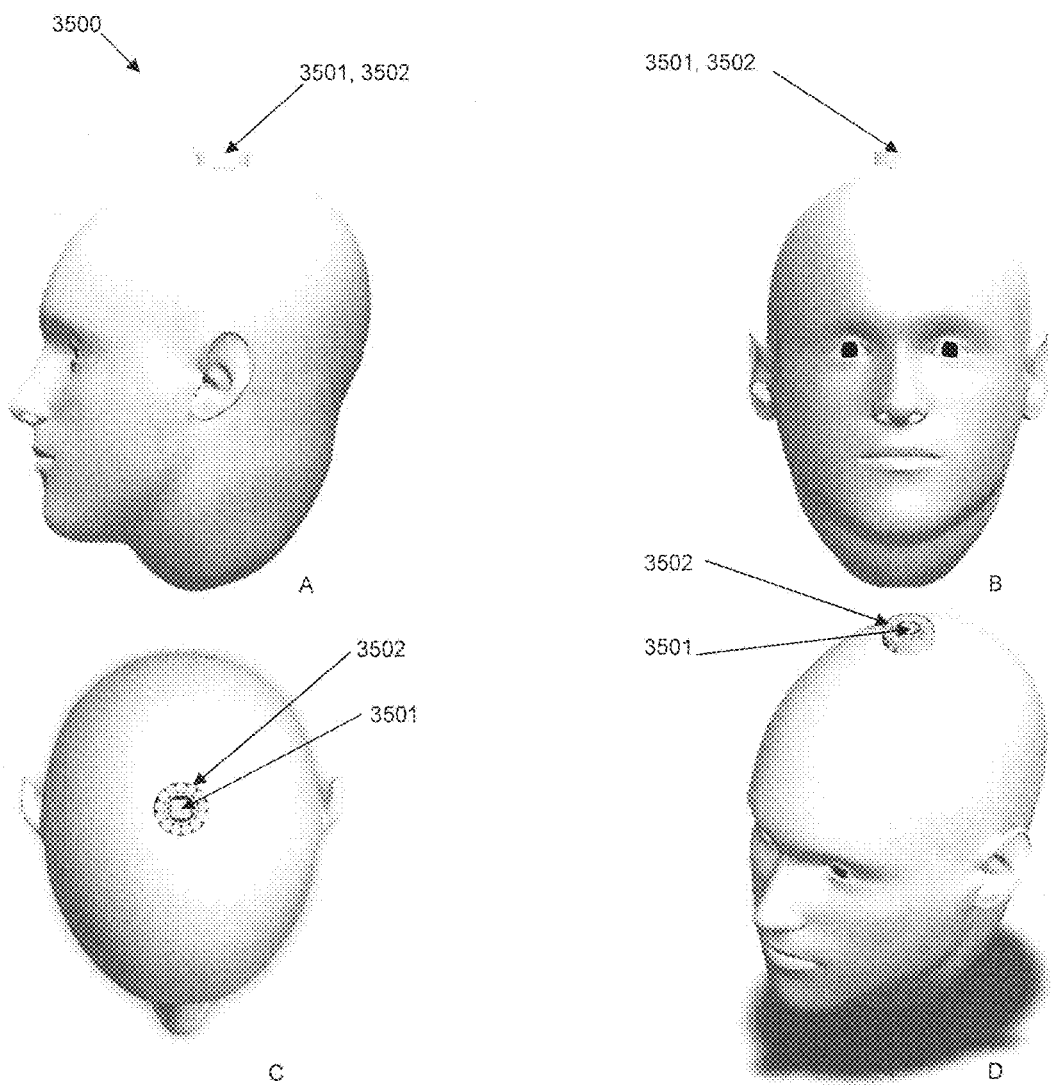
FIGS. 35A, 35B, 35C, and 35D are side, front, top, and perspective diagrams of an externally-mounted E-BNC module, in accordance with some embodiments.

FIG. 34 is a radio block diagram for a receiving apparatus for wirelessly communicating with a wireless E-BNC, in accordance with some embodiments. Once a signal is received from the E-BNC at antenna 3401, it is passed to low noise amplifier 3402, multiplexer 3403, balun 3404, gain control 3405, band pass filter 3406, balun 3407, and amplifier 3408 before going to splitter 3409. The two signals which are split are recombined at multiplexer 3410, wherein one signal has been delayed such that its phase is offset from the other signal. The signal path continues through low pass filters 3411 and 3412, going into op-amp 3413. A fraction of the signal is fed back via integrator 3414 and summer 3415 through oscillator 3416, entering the signal path at multiplexer 3403. The main signal continues through data recovery 3417 and enters a serial device that contains a microcontroller 3417, FPGA 3418, SDRAM 3419, and USB interface 3420, for connecting to computer 3421. An output of the microcontroller 3417 is sent to DAC 3422 to be fed back into the signal via summer 3415.

FIGS. 35A, 35B, 35C, and 35D are side, front, top, and perspective diagrams of a E-BNC module externally mounted on a human head, in accordance with some embodiments. As the diagrams show, device core 3501 and batteries 3502 are external to the body, and device core 3501 is connected to a pedestal and a microelectrode array (not shown) that are partially or wholly implanted beneath the skin. As FIGS. 35A and 35B make clear, device core 3501 sits above the scalp with a varying level of clearance with the scalp depending on the degree to which the user tightens the device core on its screw mating with the pedestal.

Figure 36:
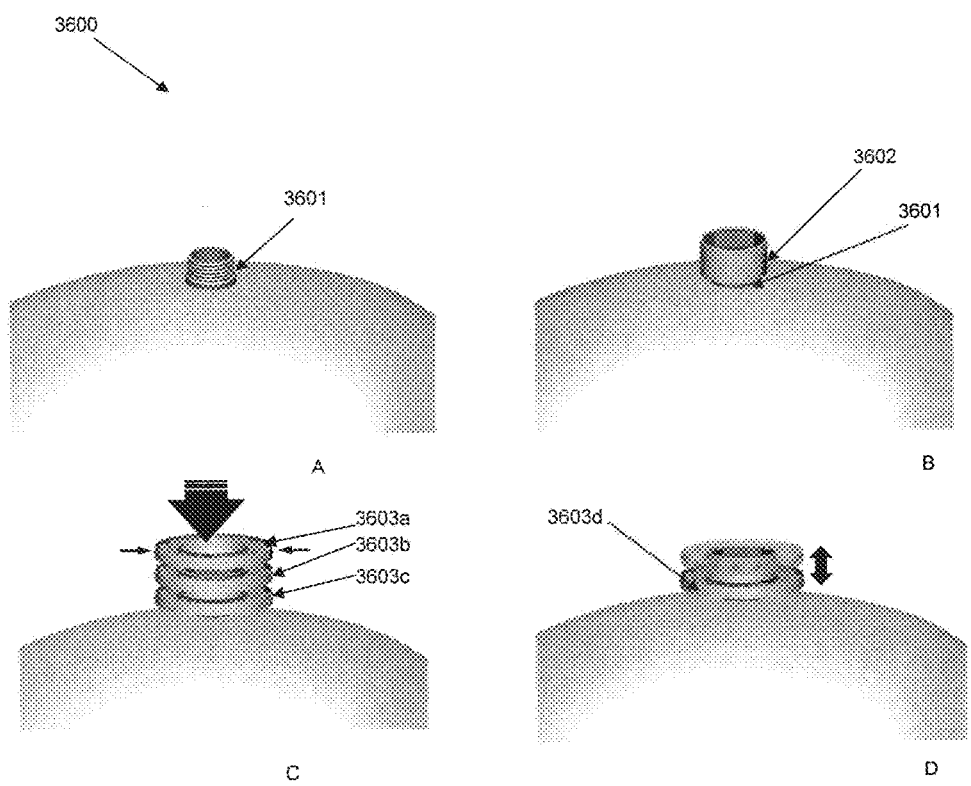
FIGS. 36A, 36B, 36C, and 36D are process diagrams showing the installation of batteries on an externally-mounted E-BNC module, in accordance with some embodiments.

FIGS. 36A, 36B, 36C, and 36D are process diagrams showing the installation of batteries on an externally-mounted E-BNC module, in accordance with some embodiments. FIG. 36A shows a pedestal 3601 without device core module. FIG. 36B shows a pedestal 3601 attached to device core module 3602. FIG. 36C shows a pedestal 3601 attached to device core module 3602, which is also attached to three battery packs 3603a, 3603b, 3603c. The arrows in the figure represent forces needed to install the battery packs. Some force is needed to depress the ball locks from the outside of the battery packs, and a small force is needed to slide the battery pack onto device core module 3602. FIG. 36D shows the adjustment of height of a battery pack 3603d in order to position it at a height relative to the skin or scalp that is conducive to comfort for the user.

The foregoing has outlined some of the more pertinent features of the subject matter. These features should be construed to be merely illustrative. Many other beneficial results can be attained by applying the disclosed subject matter in a different manner or by modifying the subject matter as will be described. For example, the elements of the SBNC may be provided in an embodiment of the E-BNC system, or vice versa.

The invention claimed is:

1. An implantable system for providing an electrical interface to a body, comprising:
   an implantable electrode array, implantable within a body and capable of providing a plurality of communication channels for communicating electrical signals detected in a body;
   an interface board coupled to the electrode array for providing a fan-out of electrical wires to a plurality of electrical contacts;
   an amplifier board in stacked relationship with the interface board, the amplifier board having an amplifier circuit coupled with the plurality of electrical contacts for processing electrical signals received from the electrode array into data signals;
   a wireless transceiver board, the wireless transceiver board having a wireless transceiver coupled to the amplifier circuit for sending and receiving telemetry data between the amplifier circuit and a wireless receiver located outside of the body;
   an electromagnetic shield disposed between the amplifier board and the wireless transceiver board, the electromagnetic shield configured to reduce unwanted crosstalk between the amplifier board and the wireless transceiver board;
   a sealed enclosure that houses the amplifier circuit and the wireless transmitter and is biocompatible with surrounding tissue, wherein the electromagnetic shield is entirely enclosed within the sealed enclosure; and
   a window within the enclosure that is transparent to a wireless medium used by the wireless transceiver,
   wherein the wireless transceiver is capable of sending data from the plurality of communication channels.

2. The implantable system of claim 1, the wireless transceiver comprising one of a radio frequency transceiver and an optical transceiver.

3. The implantable system of claim 1, wherein the wireless transceiver includes both a radio frequency transceiver and an optical transceiver.

4. The implantable system of claim 1, wherein the wireless transceiver is capable of sending real-time data from each of the plurality of channels.

5. The implantable system of claim 1, wherein the amplifier circuit is capable of processing detected electrical signals in the range of 0.1 Hz to 10 kHz for transmission by the wireless transceiver.

6. The implantable system of claim 1, wherein the wireless transceiver is for receiving data from an external wireless device, and wherein the implantable system further comprises a stimulation circuit for applying the received data to the electrode array to stimulate neurons.

7. The implantable system of claim 1, further comprising at least one light-emitting diode observable through the transparent window.

8. The implantable system of claim 1, wherein the implantable electrode array is for insertion into a brain and is capable of detecting electrical signals generated by a plurality of neurons.

9. The implantable system of claim 1, wherein the implantable electrode array is capable of detecting electrical signals in the range of 0.1 Hz to 10 kHz.

10. The implantable system of claim 1, further comprising a rechargeable battery housed within the sealed enclosure.

11. The implantable system of claim 10, further comprising an antenna for receiving wireless power and a charging circuit for charging the battery with the received wireless power.

12. The implantable system of claim 1, further comprising means for wirelessly powering the implantable system from a power source located external to the implant system.

13. The implantable system of claim 1, the electrode array comprising at least 10 electrodes.

14. The implantable system of claim 13, wherein the electrode array comprises at least 50 electrodes.

15. The implantable system of claim 12, further comprising an external charging assembly for transmitting one of power and data to the sealed enclosure via wireless transmission.

* * * * *